US010614916B1

(12) United States Patent
Einav et al.

(10) Patent No.: US 10,614,916 B1
(45) Date of Patent: Apr. 7, 2020

(54) MEANS AND METHODS FOR PROVIDING A CONTINUOUS PHARMACEUTICAL OPERATION SERVICE

(71) Applicant: Tech Pharmacy Services, LLC, Fort Lee, NJ (US)

(72) Inventors: Omer Einav, Kfar-Monash (IL); Doron Shabanov, Tzur-Yigal (IL); Yuval Siman, Ramat-HaSharon (IL); Tamir Ben David, Tel-Aviv (IL); Anthony Joseph Spero, Queensbury, NY (US); Eyal Livschitz, Givat Shmuel (IL); Thomas A. McKinney, Boonton, NJ (US); Moshe Liberman, Yehud (IL)

(73) Assignee: Tech Pharmacy Services, LLC, Fort Lee, NJ (US)

( * ) Notice: Subject to any disclaimer, the term of this patent is extended or adjusted under 35 U.S.C. 154(b) by 0 days.

(21) Appl. No.: 16/379,831

(22) Filed: Apr. 10, 2019

(51) Int. Cl.
| | | |
|---|---|---|
| *G16H 40/20* | (2018.01) | |
| *G06Q 10/08* | (2012.01) | |
| *G16H 10/60* | (2018.01) | |
| *G16H 20/13* | (2018.01) | |
| *B65B 35/10* | (2006.01) | |
| *B65B 1/30* | (2006.01) | |

(52) U.S. Cl.
CPC ............ *G16H 40/20* (2018.01); *G06Q 10/087* (2013.01); *G16H 10/60* (2018.01); *G16H 20/13* (2018.01); *B65B 1/30* (2013.01); *B65B 35/10* (2013.01)

(58) Field of Classification Search
CPC ........ G16H 40/20; G16H 20/13; G16H 10/60; G06Q 10/087; B65B 1/30; B65B 35/10
See application file for complete search history.

(56) References Cited

U.S. PATENT DOCUMENTS

| | | |
|---|---|---|
| 7,698,019 B2 | 4/2010 | Moncrief et al. |
| 8,280,550 B2 | 10/2012 | Levy et al. |
| (Continued) | | |

FOREIGN PATENT DOCUMENTS

| | | |
|---|---|---|
| WO | WO 2018/052160 | 3/2018 |

OTHER PUBLICATIONS

Restriction Official Action dated Apr. 2, 2019 From the U.S. Patent and Trademark Office Re. U.S. Appl. No. 16/214,081. (6 pages).

*Primary Examiner* — Yuhui R Pan

(57) ABSTRACT

An aspect of some embodiments of the invention relates to a pharmaceutical dispensing machine configured to perform a pharmaceutical dispensing process, comprising: at least one module configured in a first configuration to perform at least one first part of said pharmaceutical dispensing process; dispensing hardware configured in a second configuration to perform at least one second part of said pharmaceutical dispensing process; and circuitry, which controls and coordinates the operation of said at least one module and said dispensing hardware using at least one parameter related to said dispensing pharmaceutical process; wherein said at least one first part of said pharmaceutical dispensing process and said at least one second part of said pharmaceutical dispensing process overlap in functionality by at least one subassembly component in said dispensing hardware which overlaps in functionality with said dispensing module in said pharmaceutical dispensing process and are performed at a same dispensing event.

29 Claims, 24 Drawing Sheets

(56) References Cited

U.S. PATENT DOCUMENTS

| | | | |
|---|---|---|---|
| 2012/0004770 A1* | 1/2012 | Ooyen | G07F 11/58 |
| | | | 700/235 |
| 2013/0123977 A1 | 5/2013 | Sanders et al. | |
| 2013/0240555 A1 | 9/2013 | Kim | |
| 2016/0132404 A1* | 5/2016 | Munson | G07F 19/20 |
| | | | 714/4.12 |
| 2018/0122177 A1 | 5/2018 | Este et al. | |

\* cited by examiner

106

114d

114/115

108

158

MEANS AND METHODS FOR PROVIDING A CONTINUOUS PHARMACEUTICAL OPERATION SERVICE

FIELD AND BACKGROUND OF THE INVENTION

The present invention, in some embodiments thereof, relates to a pharmaceutical operation service and, more particularly, but not exclusively, to means and methods for providing a continuous pharmaceutical operation service.

Additional background art includes U.S. Pat. No. 7,698,019 discloses "a system, software and related methods of enhanced pharmaceutical operations in long term care facilities. An embodiment of a system includes a long-term care facility pharmacy group management server, long-term care facility pharmacy management software associated with the long-term care facility pharmacy group management server to manage pharmacological operations in a plurality of long-term care facilities, a plurality of pharmaceutical storage and electronic dispensing carts each positioned in a long-term care facility remote from the long-term care facility pharmacy group management server and in communication therewith, a remote pharmacy group server in communication with the long-term care facility pharmacy group management server, and a plurality of pharmaceutical prescription document processors each positioned in a long-term care facility and in communication with the remote pharmacy group server or the long-term care facility pharmacy group management server".

US patent application No. 20130123977 discloses "systems and methods for managing canisters used to automatically dispense medication. Canisters are configurable via a design process and a build process to accurately dispense a variety of medications. Design profiles are created and stored by a canister management system, and are federated to workstations used to build and fill the canisters, and to workstations used to dispense the medication. Information related to the build process, the fill process, and the dispense process is also federated by the system. The system also enables the transmission of other types of messages between client applications on the workstations and the canister management system. The system is useful to federate data regardless of a structure of a supply chain used to design, build, distribute, and use the canisters".

US patent application No. 20130240555 discloses "a tablet cassette of a medicine packing apparatus capable of sensing the tablet congestion occurred inside the tablet cassette and settling the congestion and a method for operating the same are provided. The tablet cassette includes a cartridge having space for containing tablets and an outlet for discharging the tablets, a tablet installation unit, and an oscillator vibrating the cartridge when tablets may not be discharged even if they are remained inside the cartridge".

International patent application No. WO2018052160 discloses "a medication dispenser having high space utilization, having a large quantity of medication packages loaded therein, having high medication-dispensing efficiency, and enabling smooth dispensing regardless of the size and type of the medication package. Provided is the medication dispenser comprising: a canister module in which a canister having the medication packages loaded therein is accommodated; and a pickup robot for picking up the medication packages in individual units, wherein the canister includes: L-shaped first and second walls for providing a loading space allowing the medication packages to move therein in the long axis direction of the canister; a guide for moving the first wall toward the second wall so as to adjust a gap with the second wall; a contact plate moving along the loading space, and bringing the medication packages into close contact with each other by pressure; and a spiral spring providing the pressure to the contact plate, having a strip shape, and wound in a coil shape".

US patent application No. 20180122177 discloses "storage and distribution system for products in unit doses, including a plurality of housing units, each including a plurality of locations for products in unit doses. The housing units are organized on a vertical plane to produce at least one portion of a picking wall, in which the locations for products in unit doses face selective picking members. A picking unit includes picking members oriented on the picking wall for picking products packaged in unit doses. A collecting unit, arranged on a second side of the picking unit, includes a rack having a plurality of pegs facing towards the first side of the picking unit. The pegs are reached by the picking members so as to pick therefrom or deposit thereon products packaged in unit doses. The plurality of pegs as a whole can collect a smaller number of unit dose products than those that can be stored in the automatic store".

U.S. Pat. No. 8,280,550 discloses "devices, systems, and methods for remotely managing items that are configured to be stored in at least one dispensing device. This includes receiving user identification information at a host computer system from an electronic device that is remotely located from the dispensing device. This also includes transmitting from the host computer system to the electronic device a disposition of at least one item, wherein the at least one item is associated with a patient. Further, this includes receiving, at the host computer system from the remote electronic device, information about the item originating from the dispensing device, wherein the information includes a further disposition of the item".

SUMMARY OF THE INVENTION

According to an aspect of some embodiments of the present invention there is provided a pharmaceutical dispensing machine configured to perform a pharmaceutical dispensing process including recovering at least one pharmaceutical from a dedicated container, relaying said at least one pharmaceutical to the inside of at least one pharmaceutical carrier package, closing and labeling said at least one pharmaceutical carrier package, and dispensing said at least one pharmaceutical inside said at least one pharmaceutical carrier package, comprising: at least one module configured in a first configuration to perform at least one first part of said pharmaceutical dispensing process; dispensing hardware configured in a second configuration to perform at least one second part of said pharmaceutical dispensing process; and circuitry, which controls said recovering at least one pharmaceutical from a dedicated container, relaying said at least one pharmaceutical to the inside of at least one pharmaceutical carrier package, closing and labeling said at least one pharmaceutical carrier package, and dispensing said at least one pharmaceutical inside said at least one pharmaceutical carrier package; including coordinating the operation of said at least one module and said dispensing hardware using at least one parameter related to said dispensing pharmaceutical process; wherein said at least one first part of said pharmaceutical dispensing process and said at least one second part of said pharmaceutical dispensing process overlap in functionality by at least one subassembly component in said dispensing hardware, which overlaps in functionality with said dispensing module in said pharmaceutical dispensing process, and are performed at a same dispensing event.

According to some embodiments of the invention, said at least one first part of said pharmaceutical dispensing process and said at least one second part of said pharmaceutical dispensing process are different parts of said pharmaceutical dispensing process.

According to some embodiments of the invention, said at least one first configuration and said at least one second configuration are the same configuration.

According to some embodiments of the invention, said at least one first configuration and said at least one second configuration are different configurations.

According to some embodiments of the invention, said at least one first and said at least one second configuration are adapted for at least one parameter selected from the group consisting of:
  a. type of pharmaceuticals;
  b. size of pharmaceuticals;
  c. quantity of pharmaceuticals;
  d. type of pharmaceutical carrier packages;
  e. size of pharmaceutical carrier packages;
  f. engaging mechanism of pharmaceuticals; and
  g. transporting mechanism of pharmaceuticals.

According to some embodiments of the invention, said at least one first part of said pharmaceutical dispensing process and said at least one second part of said pharmaceutical dispensing process are performed at the same time.

According to some embodiments of the invention, said at least one first part of said pharmaceutical dispensing process and said at least one second part of said pharmaceutical dispensing process are performed at different times.

According to some embodiments of the invention, said at least one module is selected from a group consisting of: a pharmaceutical array module, a pharmaceutical tote module, a pharmaceutical operational modules section and a mechanical arm module.

According to some embodiments of the invention, said pharmaceutical is recovered from said pharmaceutical array module by said mechanical arm module.

According to some embodiments of the invention, said pharmaceutical is transported to an envelope located in an envelope module in said operational modules sections by said mechanical arm module.

According to some embodiments of the invention, said pharmaceutical dispensing process comprises at least one of the following:
  a. inserting more than one pharmaceutical into one envelope;
  b. inserting more than one type of pharmaceutical into one envelope;
  c. inserting one type of pharmaceutical in more than one envelope.

According to some embodiments of the invention, said dispensing hardware is operated when said at least one module cannot be operated.

According to some embodiments of the invention, said at least one module comprises at least one unit configured in a third configuration to perform at least one third part of said process; and said at least one unit comprises at least one element configured in a fourth configuration to perform at least one fourth part of said process.

According to some embodiments of the invention, modules, hardware, units and elements comprise at least one additional hardware in communication with said circuitry and configured to monitor part of said process, selected from the group consisting of:
  a. at least one sensor; and
  b. at least one camera;
said at least one additional hardware is activated remotely by a user via a dedicated server.

According to some embodiments of the invention, modules are configured to be independently dismounted from said pharmaceutical dispensing device; and wherein dismounting said modules does not interrupt the part of said process of said pharmaceutical dispensing machine.

According to some embodiments of the invention, modules are configured to be independently replaced from said pharmaceutical dispensing device.

According to some embodiments of the invention, replacing said modules does not interrupt the part of said process of said pharmaceutical dispensing machine.

According to some embodiments of the invention, disconnecting between said modules and said pharmaceutical dispensing machine when replacing said modules takes from about 1 second to about 10 minutes.

According to some embodiments of the invention, said at least one module is activated at the middle of said pharmaceutical dispensing process.

According to some embodiments of the invention, said at least one dispensing hardware is activated at the middle of said pharmaceutical dispensing process.

According to some embodiments of the invention, said module is a removable module.

According to an aspect of some embodiments of the present invention there is provided a method of operating a pharmaceutical dispensing device comprising: providing a pharmaceutical dispensing device with at least one first removable pharmaceutical dispensing module, at least one second removable pharmaceutical dispensing module and circuitry interconnecting, controlling and coordinating mechanical operations in a pharmaceutical dispensing process of said first and said second removable pharmaceutical dispensing modules using at least one parameter related to dispensing pharmaceuticals; configuring, before a dispensing event, said at least one second removable pharmaceutical dispensing module to perform a mechanical operation of said at least one first removable pharmaceutical dispensing module; mechanically operating said first and said second removable pharmaceutical dispensing modules at a same dispensing event; and continuing mechanically operating, during the same dispensing event, one of said modules when the other cannot operate.

According to some embodiments of the invention, said first and said second removable pharmaceutical dispensing modules from a group consisting of: a pharmaceutical array module, a pharmaceutical tote module, a pharmaceutical operational modules section and a mechanical arm module.

According to some embodiments of the invention, said pharmaceutical dispensing process comprises:
  a. storing at least one pharmaceutical;
  b. receiving information of at least one pharmaceutical to be dispensed;
  c. identifying said at least one pharmaceutical;
  d. identifying at least one location of said at least one pharmaceutical;
  e. collecting said at least one pharmaceutical from said at least one location;
  f. transporting said at least one pharmaceutical from said at least one location to at least one secondary location in said dispensing machine;
  g. releasing said at least one pharmaceutical in said at least one secondary location;
  h. printing at least one information on at least one pharmaceutical transporting container;
  i. closing said at least one pharmaceutical transporting container;
  j. inserting said at least one container in at least one tote; and
  k. dispensing said at least one tote to at least one authorized user.

According to some embodiments of the invention, said at least one parameter or said mechanical operation is selected from the group consisting of:

a. storing at least one pharmaceutical;

a. identifying at least one pharmaceutical;

b. identifying at least one location of said at least one pharmaceutical;

c. collecting said at least one pharmaceutical from said at least one location;

d. transporting said at least one pharmaceutical from said at least one location to at least one secondary location in said dispensing machine;

e. releasing said at least one pharmaceutical in said at least one secondary location;

f. printing at least one information on at least one pharmaceutical transporting container;

g. closing said at least one pharmaceutical transporting container;

h. inserting said at least one container in at least one tote; and i. dispensing said at least one tote to at least one authorized user;

According to some embodiments of the invention, said at least one location is located in said pharmaceutical array module.

According to some embodiments of the invention, said transporting is performed by said mechanical arm module.

According to some embodiments of the invention, said at least one secondary According to some embodiments of the invention, said pharmaceutical transporting container is an envelope.

According to some embodiments of the invention, said method comprises at least one of the following:

a. inserting more than one pharmaceutical into one envelope;

b. inserting more than one type of pharmaceutical into one envelope;

c. inserting one type of pharmaceutical in more than one envelope.

According to an aspect of some embodiments of the present invention there is provided a pharmaceutical dispensing machine configured to perform a pharmaceutical dispensing process including recovering at least one pharmaceutical from a dedicated container, relaying said at least one pharmaceutical to the inside of at least one pharmaceutical carrier package, sealing and labeling said at least one pharmaceutical carrier package, and dispensing said at least one pharmaceutical inside said at least one pharmaceutical carrier package, comprising:

a. at least one module including a first configuration configured to perform at least one first part of said process;

b. dispensing hardware including a second configuration configured to perform at least one second part of said process; and c. circuitry, which coordinates the operation of, said at least one module and said dispensing hardware using at least one parameter related to dispensing pharmaceuticals;

wherein said at least one first part of said process and said at least one second part of said process overlap in functionality in said process and are performed at a same dispensing event.

According to some embodiments of the invention, said at least one first part of said process and said at least one second part of said process are different parts of said process.

According to some embodiments of the invention, said at least one first configuration and said at least one second configuration are the same configuration.

According to some embodiments of the invention, said at least one first configuration and said at least one second configuration are different configurations.

According to some embodiments of the invention, said at least one first part of said process and said at least one second part of said process are performed at the same time.

According to some embodiments of the invention, said at least one first part of said process and said at least one second part of said process are performed at different times.

According to some embodiments of the invention, said at least one module is selected from a group consisting of: a pharmaceutical array module, a pharmaceutical tote module, a pharmaceutical operational modules section and a mechanical arm module.

According to some embodiments of the invention, said dispensing hardware is operated when said at least one module cannot be operated.

According to some embodiments of the invention, said at least one module comprises at least one first unit including a third configuration configured to perform at least one third part of said process.

According to some embodiments of the invention, said at least one module comprises at least one second unit including a fourth configuration configured to perform at least one fourth part of said process.

According to some embodiments of the invention, said at least one third part of said process and said at least one fourth part of said process are the same part of said process.

According to some embodiments of the invention, said at least one third part of said process and said at least one fourth part of said process are different part of said process.

According to some embodiments of the invention, said at least one third configuration and said at least one fourth configuration are the same configuration.

According to some embodiments of the invention, said at least one third configuration and said at least one fourth configuration are different configurations.

According to some embodiments of the invention, said at least one third part of said process and said at least one fourth part of said process are performed at the same time.

According to some embodiments of the invention, said at least one third part of said process and said at least one fourth part of said process are performed at different times.

According to some embodiments of the invention, said at least one unit comprises at least one first element including a fifth configuration configured to perform at least one fifth part of said process.

According to some embodiments of the invention, said at least one unit comprises at least one second element including a sixth configuration configured to perform at least one sixth part of said process.

According to some embodiments of the invention, said at least one fifth part of said process and said at least one sixth part of said process are the same part of said process.

According to some embodiments of the invention, said at least one fifth part of said process and said at least one sixth part of said process are different part of said process.

According to some embodiments of the invention, said at least one fifth configuration and said at least one sixth configuration are the same configuration.

According to some embodiments of the invention, said at least one fifth configuration and said at least one sixth configuration are different configurations.

According to some embodiments of the invention, said at least one fifth part of said process and said at least one sixth part of said process are performed at the same time.

According to some embodiments of the invention, said at least one fifth part of said process and said at least one sixth part of said process are performed at different times.

According to some embodiments of the invention, modules, hardware, units and elements comprise at least one sensor in communication with said circuitry and configured to monitor part of said process.

According to some embodiments of the invention, modules, hardware, units and elements comprise at least one camera in communication with said circuitry and configured to visually monitor part of said process.

According to some embodiments of the invention, said at least one sensor and said at least one camera are activated remotely by a user via a dedicated server.

According to some embodiments of the invention, modules, hardware, units and elements are configured to be independently dismounted from said pharmaceutical dispensing device.

According to some embodiments of the invention, dismounting said modules, hardware, units and elements does not interrupt the part of said process of said pharmaceutical dispensing machine.

According to some embodiments of the invention, modules, hardware, units and elements are configured to be independently replaced from said pharmaceutical dispensing device.

According to some embodiments of the invention, replacing said modules, hardware, units and elements does not interrupt the part of said process of said pharmaceutical dispensing machine.

According to some embodiments of the invention, replacing said modules, hardware, units and elements is from about 1 minute to about 10 minutes.

According to some embodiments of the invention, said pharmaceutical array module comprises a plurality of drug units.

According to some embodiments of the invention, the number of said plurality of drug units is from about 4 to about 300.

According to some embodiments of the invention, said plurality of drug units comprise a plurality of drug elements.

According to some embodiments of the invention, the number of said drug elements is from about 2 to about 200.

According to some embodiments of the invention, said plurality of drug units have a horizontal orientation with respect to said pharmaceutical array module.

According to some embodiments of the invention, said plurality of drug units have a vertical orientation with respect to said pharmaceutical array module.

According to some embodiments of the invention, said pharmaceutical tote module comprise a plurality of trays.

According to some embodiments of the invention, envelopes that have been marked, filled with pharmaceuticals, closed, crimped and ready to be dispensed are inserted in said trays.

According to some embodiments of the invention, said pharmaceutical operational module section comprises a plurality of submodules.

According to some embodiments of the invention, said plurality of submodules are selected from a group consisting of: a printer module, a crimper module, at least one envelope module and a control module.

According to an aspect of some embodiments of the present invention there is provided a method of operating a pharmaceutical dispensing device comprising:
 a. providing a pharmaceutical dispensing device with at least one first removable pharmaceutical dispensing module, at least one second removable pharmaceutical dispensing module and circuitry interconnecting and coordinating mechanical operations in a pharmaceutical dispensing process of said first and said second removable pharmaceutical dispensing modules using at least one parameter related to dispensing pharmaceuticals;
 c. configuring, before a dispensing event, said at least one second removable pharmaceutical dispensing module to perform a mechanical operation of said at least one first removable pharmaceutical dispensing module;
 d. mechanically operating said first and said second removable pharmaceutical dispensing modules at a same dispensing event;
 e. continuing mechanically operating, during the same dispensing event, one of said modules when the other cannot operate.

According to some embodiments of the invention, providing said first and said second removable pharmaceutical dispensing modules from a group consisting of: a pharmaceutical array module, a pharmaceutical tote module, a pharmaceutical operational modules section and a mechanical arm module.

According to some embodiments of the invention, said at least one parameter is storing at least one pharmaceutical.

According to some embodiments of the invention, said at least one parameter is identifying at least one pharmaceutical.

According to some embodiments of the invention, said at least one parameter is identifying at least one location of said at least one pharmaceutical.

According to some embodiments of the invention, said at least one location is located in said pharmaceutical array module.

According to some embodiments of the invention, said at least one parameter is collecting said at least one pharmaceutical from said at least one location.

According to some embodiments of the invention, said at least one parameter is transporting said at least one pharmaceutical from said at least one location to at least one secondary location in said dispensing machine.

According to some embodiments of the invention, said transporting is performed by said mechanical arm module.

According to some embodiments of the invention, said at least one secondary location is a pharmaceutical transporting container.

According to some embodiments of the invention, said pharmaceutical transporting container is an envelope.

According to some embodiments of the invention, said at least one parameter is releasing said at least one pharmaceutical in said at least one secondary location.

According to some embodiments of the invention, said at least one parameter is printing at least one information on at least one pharmaceutical transporting container.

According to some embodiments of the invention, said at least one parameter is sealing said at least one pharmaceutical transporting container.

According to some embodiments of the invention, said at least one parameter is inserting said at least one container in at least one tote.

According to some embodiments of the invention, said at least one parameter is dispensing said at least one tote to at least one authorized user.

According to some embodiments of the invention, said mechanical operation is storing at least one pharmaceutical.

According to some embodiments of the invention, said mechanical operation is identifying at least one pharmaceutical.

According to some embodiments of the invention, said mechanical operation is identifying at least one location of said at least one pharmaceutical.

According to some embodiments of the invention, said mechanical operation is collecting said at least one pharmaceutical from said at least one location.

According to some embodiments of the invention, said mechanical operation is transporting said at least one pharmaceutical from said at least one location to at least one secondary location in said dispensing machine.

According to some embodiments of the invention, said at least one secondary location is a pharmaceutical transporting container.

According to some embodiments of the invention, said pharmaceutical transporting container is an envelope.

According to some embodiments of the invention, said mechanical operation is releasing said at least one pharmaceutical in said at least one secondary location.

According to some embodiments of the invention, said mechanical operation is printing at least one information on at least one pharmaceutical transporting container.

According to some embodiments of the invention, said mechanical operation is sealing said at least one pharmaceutical transporting container.

According to some embodiments of the invention, said mechanical operation is inserting said at least one container in at least one tote.

According to some embodiments of the invention, said mechanical operation is dispensing said at least one tote to at least one authorized user.

According to an aspect of some embodiments of the present invention there is provided a method of scheduling maintenance for a pharmaceutical dispensing device, comprising:

a. receiving a request to perform said maintenance;
 b. automatically generating at least one proposed maintenance window matching production goals of said pharmaceutical dispensing device and mechanical capability of said pharmaceutical dispensing device and said maintenance and said request;
 c. responding to said request with said at least one proposed maintenance window.

According to some embodiments of the invention, said request comprises at least one preferred time window to perform said maintenance.

According to some embodiments of the invention, generating comprises comparing said at least one preferred time window to perform said maintenance with a production schedule of said pharmaceutical dispensing device.

According to some embodiments of the invention, when said generating comprises amending said production schedule to achieve said production goals to enable the generation of said at least one proposed maintenance window at said at least one preferred time window to perform said maintenance.

According to some embodiments of the invention, said amending comprises utilizing a mechanical capability from about 50% to about 100%.

According to some embodiments of the invention, said amending comprises utilizing a mechanical capability from about 100% to about 200% by activating back up pharmaceutical modules.

According to an aspect of some embodiments of the present invention there is provided a self-configuring pharmaceutical dispensing device, comprising:

(a) at least one replaceable module configured to perform part of a pharmaceutical dispensing process;
 (b) at least one additional hardware component which interfaces with said at least one replaceable module to assist in said dispensing process;
 (c) at least one identification circuit associated with said at least one replaceable module and configured to detect an indication of at least one property of said at least one replaceable module;
 (d) a control circuitry which coordinates the activities of said at least one replaceable module and said additional hardware using at least one setup parameter value; and
 (e) a configuration circuitry, which receives said detected indication and modifies said at least one setup parameter value in response to said detected indication.

According to some embodiments of the invention, said at least one replaceable module is selected from a group consisting of: a pharmaceutical array module, a pharmaceutical tote module, a pharmaceutical operational modules section and a mechanical arm module.

According to some embodiments of the invention, said dispensing process comprises storing at least one pharmaceutical.

According to some embodiments of the invention, said dispensing process comprises identifying at least one pharmaceutical.

According to some embodiments of the invention, said dispensing process comprises identifying at least one location of said at least one pharmaceutical.

According to some embodiments of the invention, said at least one location is located in said pharmaceutical array module.

According to some embodiments of the invention, wherein said dispensing process comprises collecting said at least one pharmaceutical from said at least one location.

According to some embodiments of the invention, said dispensing process comprises transporting said at least one pharmaceutical from said at least one location to at least one secondary location in said dispensing machine.

According to some embodiments of the invention, said transporting is performed by said mechanical arm module.

According to some embodiments of the invention, said at least one secondary location is a pharmaceutical transporting container.

According to some embodiments of the invention, said pharmaceutical transporting container is an envelope.

According to some embodiments of the invention, said dispensing process comprises releasing said at least one pharmaceutical in said at least one secondary location.

According to some embodiments of the invention, said dispensing process comprises printing at least one information on at least one pharmaceutical transporting container.

According to some embodiments of the invention, said dispensing process comprises sealing said at least one pharmaceutical transporting container.

According to some embodiments of the invention, said dispensing process comprises inserting said at least one container in at least one tote.

According to some embodiments of the invention, said dispensing process comprises dispensing said at least one tote to at least one authorized user.

According to some embodiments of the invention, said at least one property comprises correct functioning of said at least one replaceable module.

According to some embodiments of the invention, said at least one property comprises type of pharmaceutical.

According to some embodiments of the invention, said at least one property comprises size of pharmaceutical.

According to some embodiments of the invention, said at least one property comprises quantity of pharmaceuticals.

According to some embodiments of the invention, said at least one property comprises type of pharmaceutical transporting container.

According to some embodiments of the invention, said indication is a change in said correct functioning of said at least one replaceable module.

According to some embodiments of the invention, said indication is a change in said type of pharmaceutical.

According to some embodiments of the invention, said indication is a change in said size of pharmaceutical.

According to some embodiments of the invention, said indication is a change in said quantity of pharmaceuticals.

According to some embodiments of the invention, said indication is a change in said type of pharmaceutical transporting container.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Figure 16A:
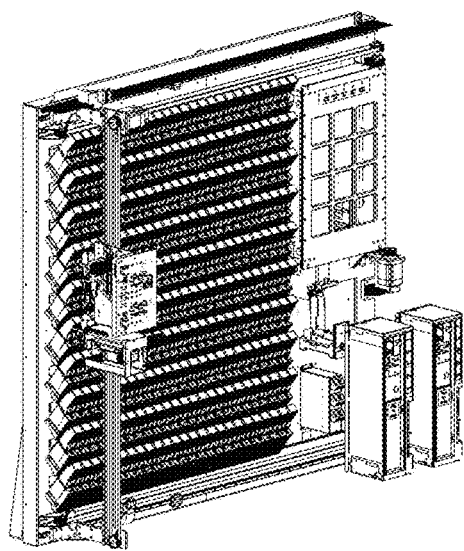
Figure 16B:
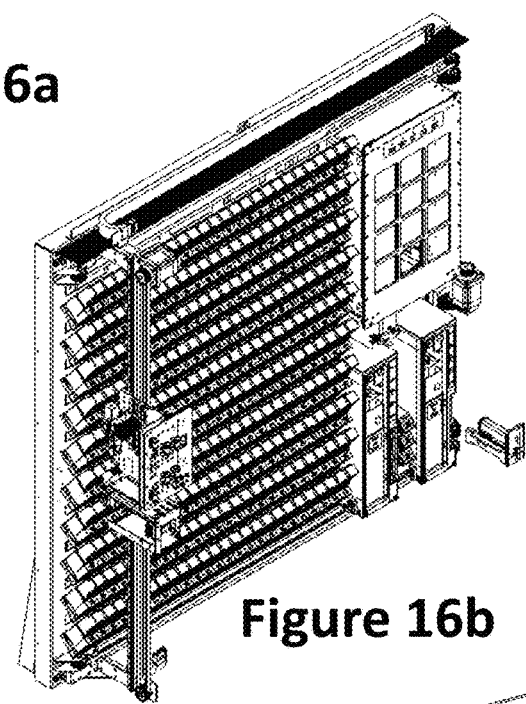
Figure 16C:
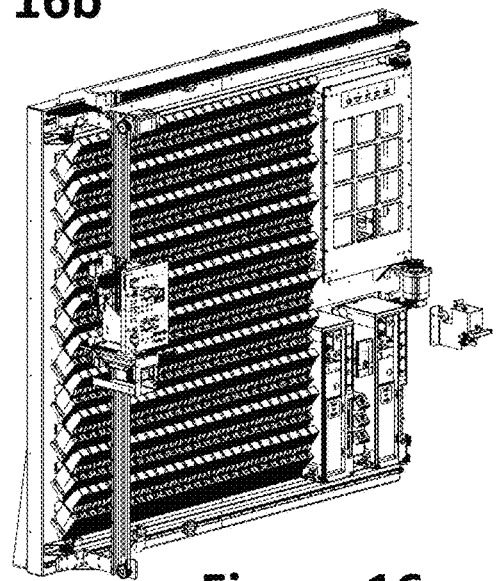
Figure 17A:
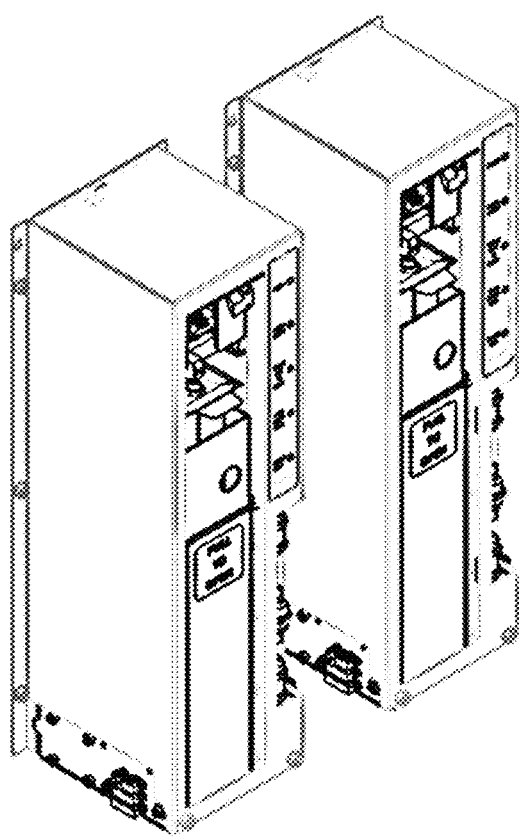
Figure 17B:
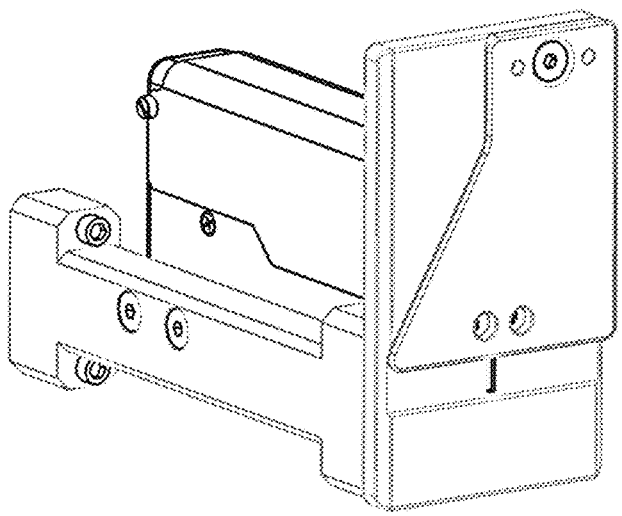
Figure 17C:
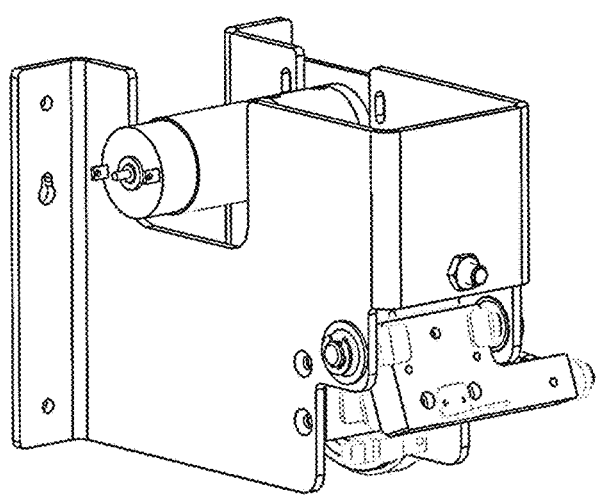
Figure 18A:
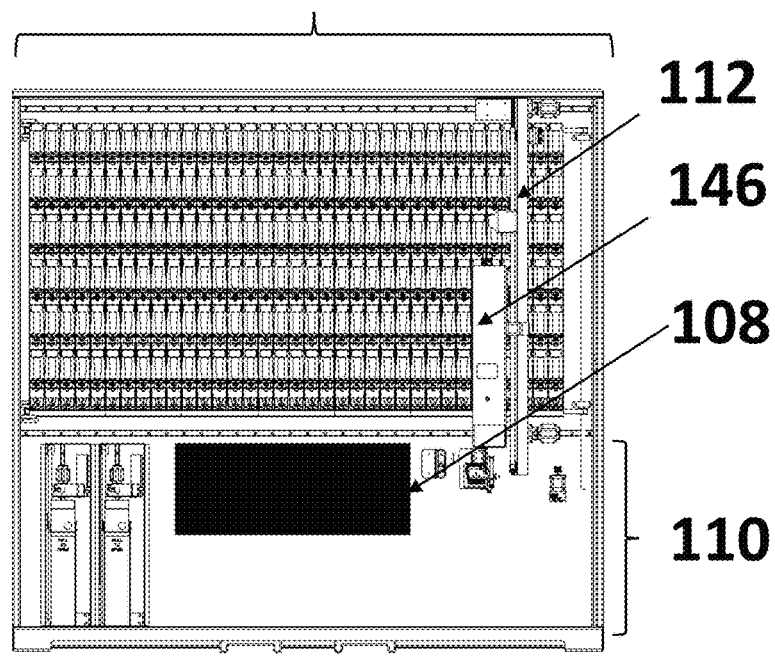
Figure 18B:
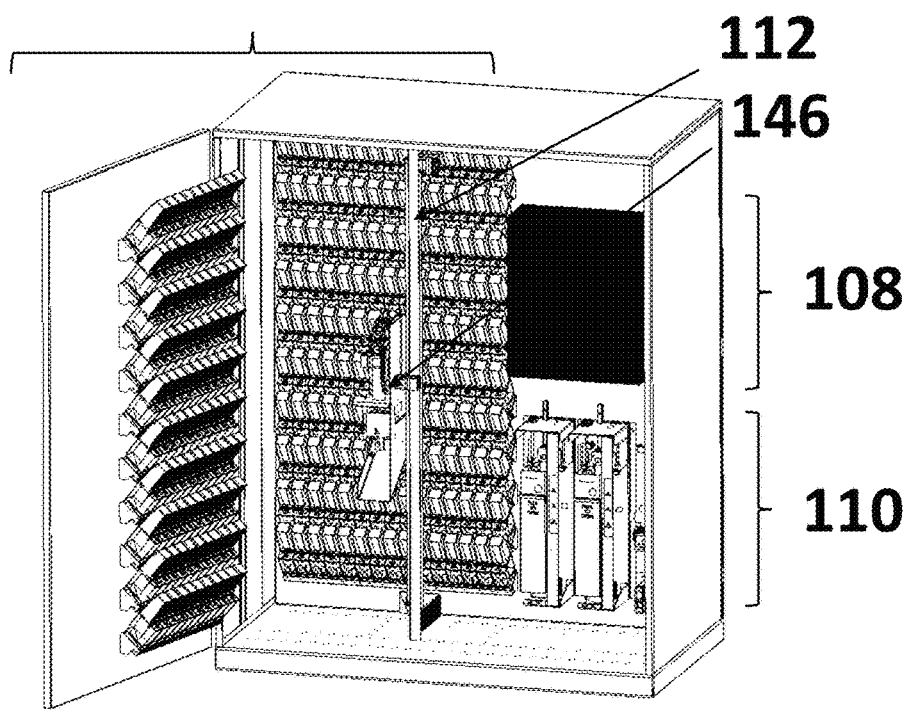
Figure 18C:
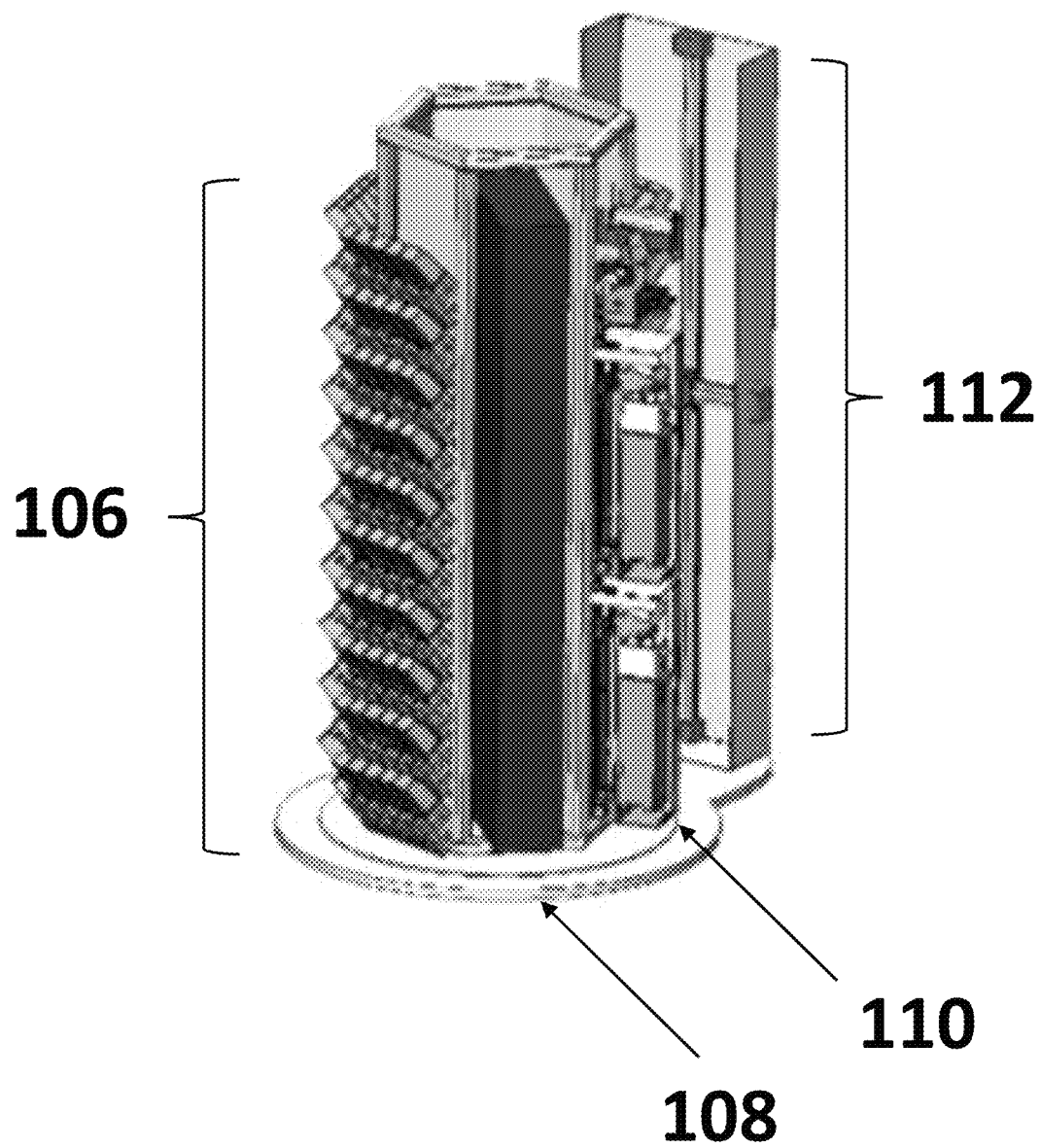
Figure 19:
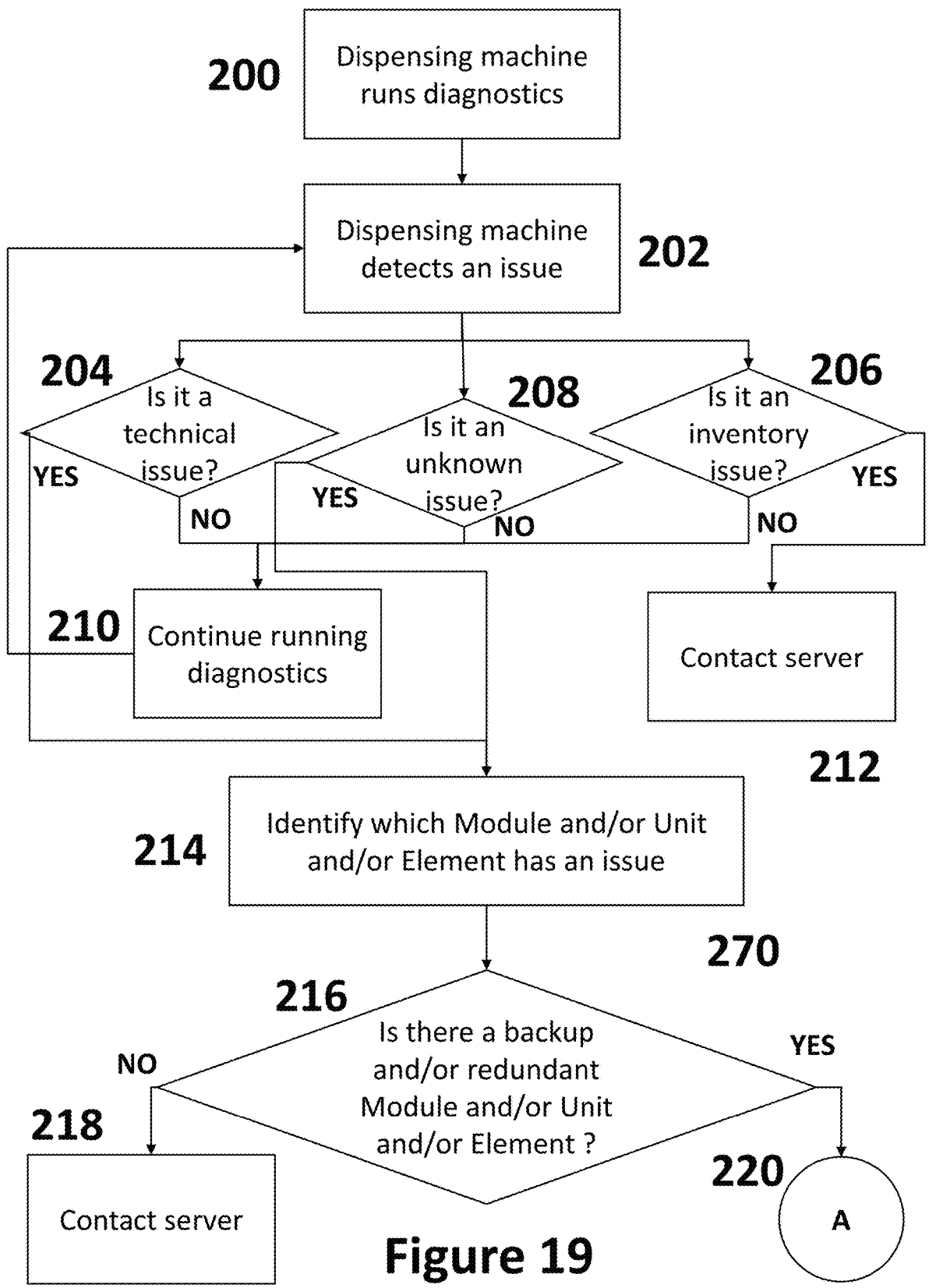
Figure 20:
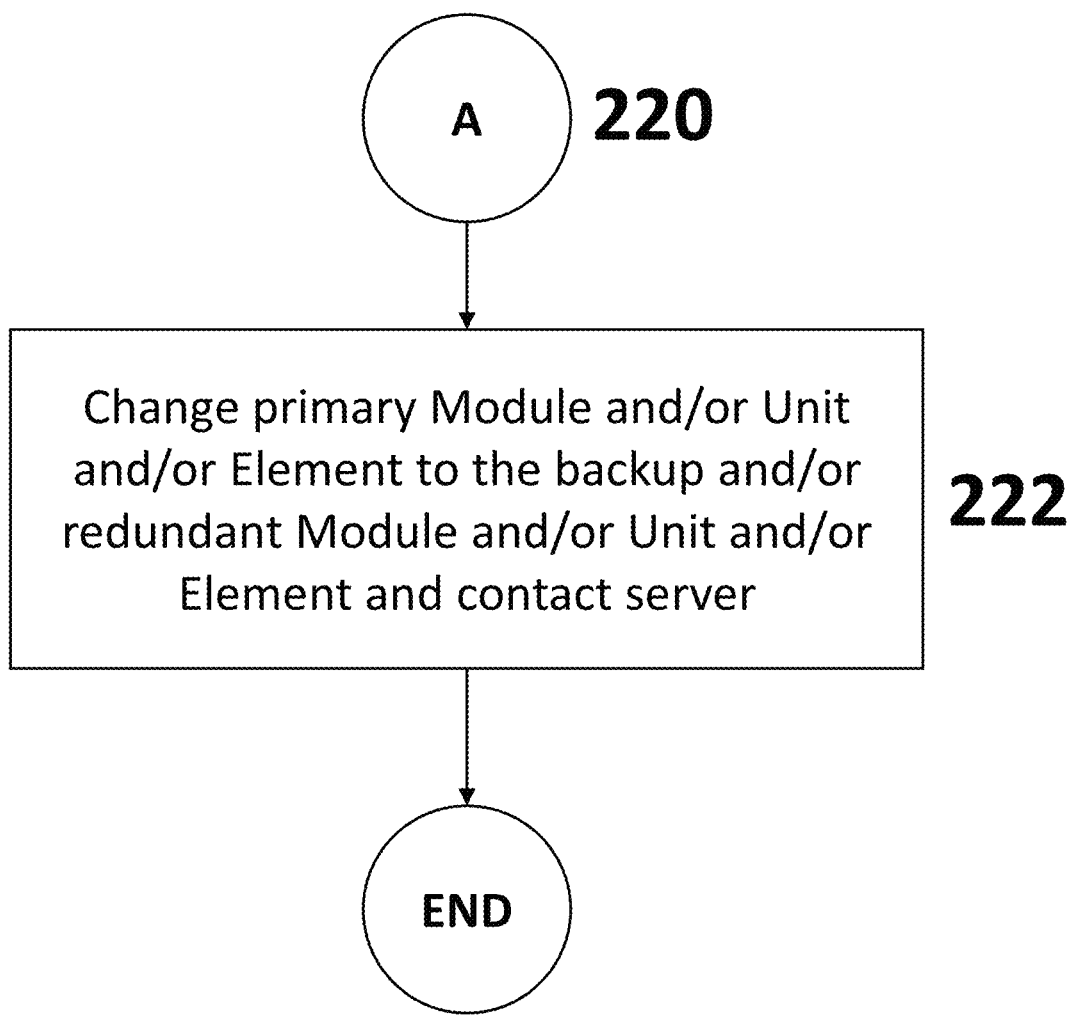
Figure 21:
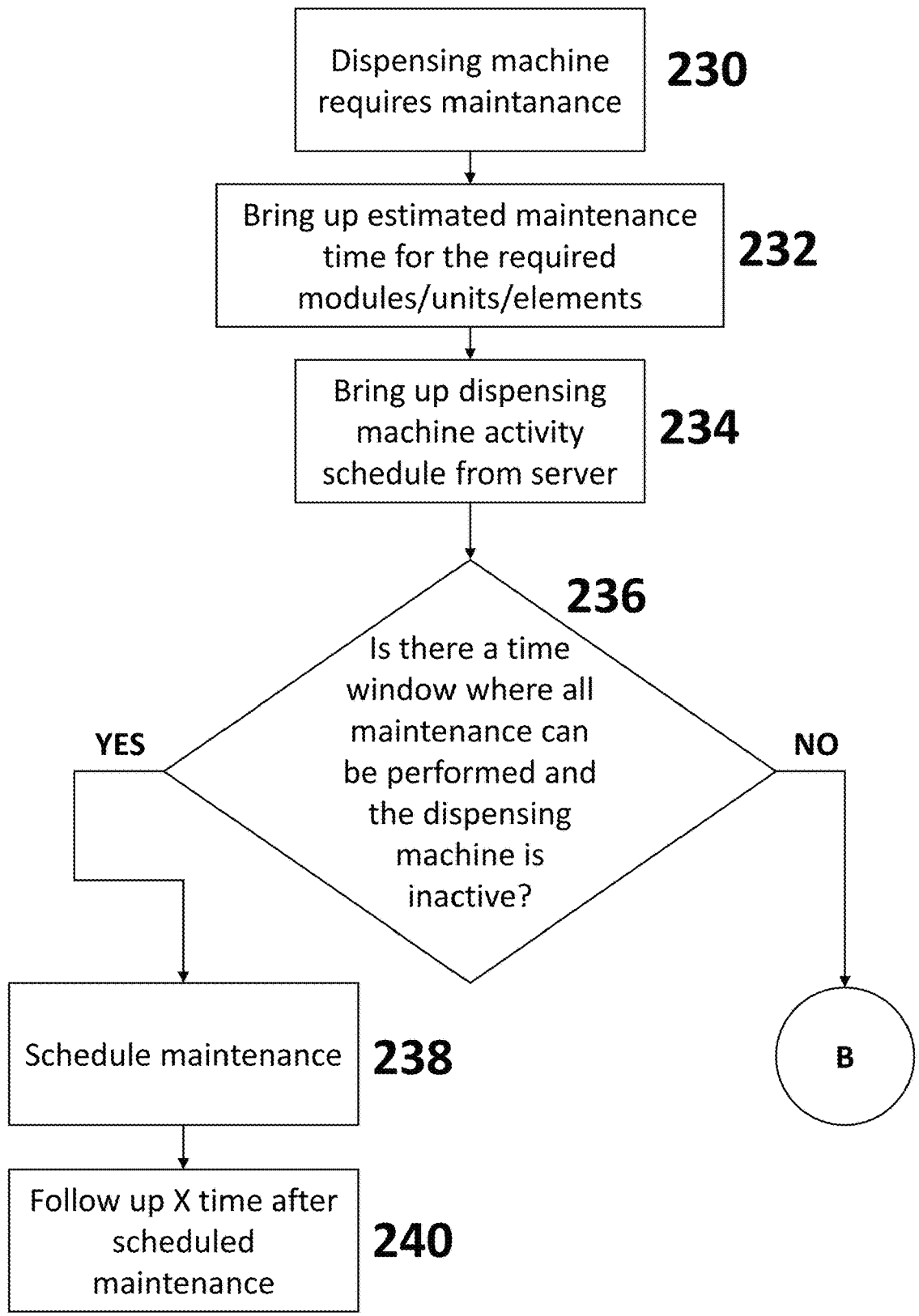
Figure 22:
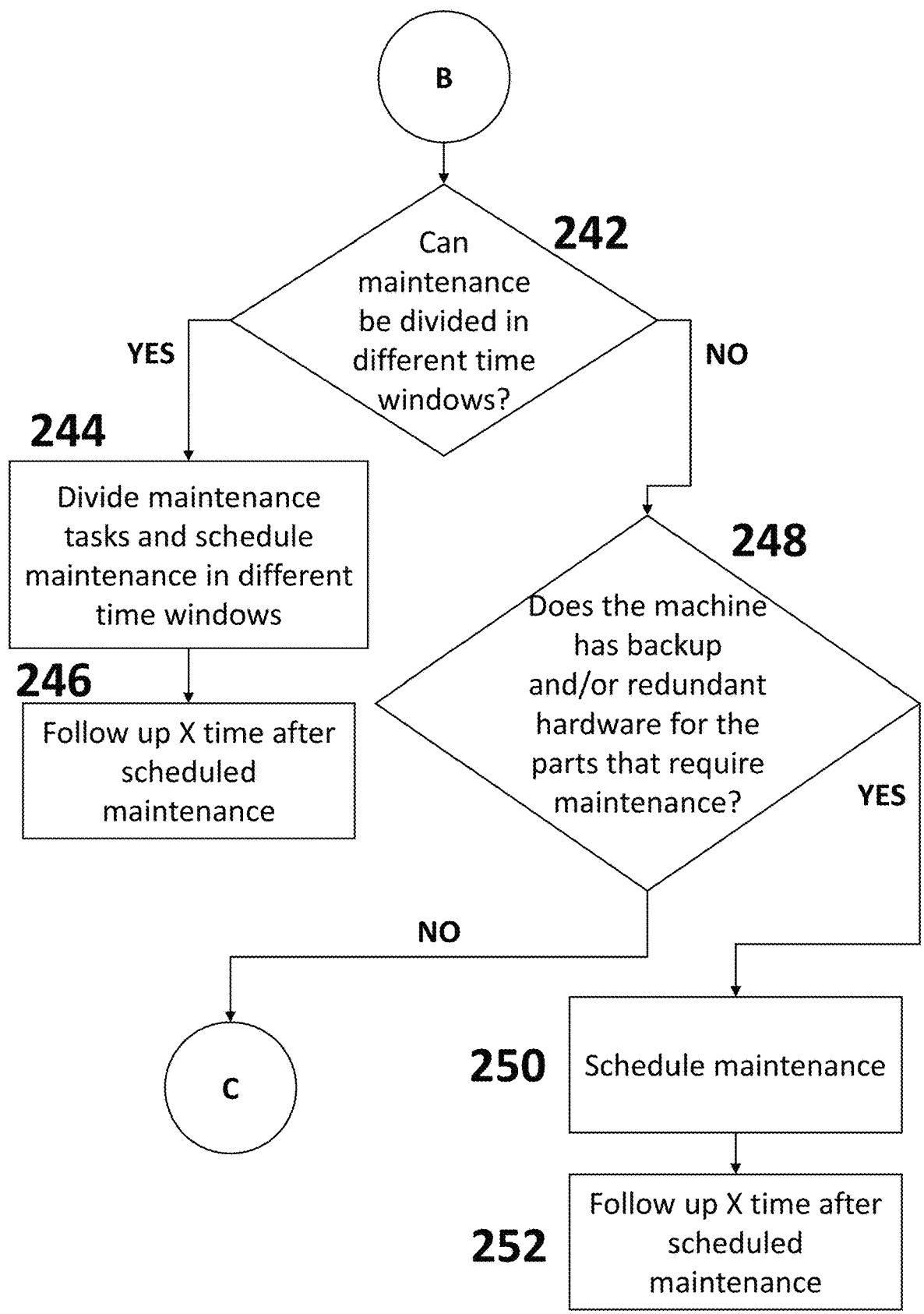
Figure 23:
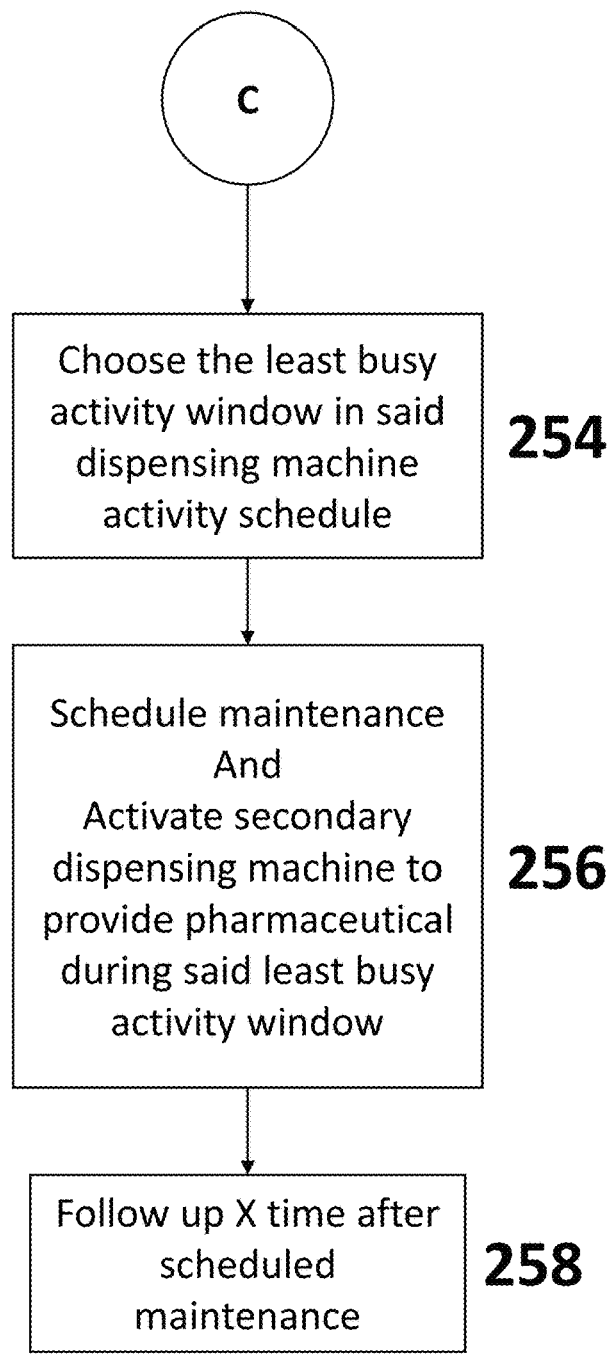

FIGS. 16a-c are three schematic representations of disconnected parts from the pharmaceutical operational modules section, according to some embodiments of the present invention;

FIGS. 17a-c are schematic representations of the envelope modules (a), printer module (b) and crimper module (c), according to some embodiments of the present invention;

FIGS. 18a-c are schematic representations of exemplary configurations of the pharmaceutical dispensing machine, according to some embodiments of the present invention;

FIGS. 19 and 20 are schematic flowcharts of a method performed by an exemplary pharmaceutical operation service system, according to some embodiments of the present invention; and FIGS. 21, 22 and 23 are schematic flowcharts of another method performed by an exemplary pharmaceutical operation service system, according to some embodiments of the present invention.

DESCRIPTION OF SPECIFIC EMBODIMENTS OF THE INVENTION

The present invention, in some embodiments thereof, relates to a pharmaceutical operation service and, more particularly, but not exclusively, to means and methods for providing a continuous pharmaceutical operation service.

Overview

An aspect of some embodiments of the invention relates to pharmaceutical dispensing machines with at least one redundant and/or backup hardware therefore providing said pharmaceutical dispensing machines with high reliability and/or easy maintainability. In some embodiments, the pharmaceutical dispensing machine comprises at least one module. In some embodiments, the pharmaceutical dispensing machine comprises a plurality of modules. In some embodiments, said at least one module is selected from a group consisting of: a pharmaceutical array module, a pharmaceutical tote module, a pharmaceutical operational modules section and a mechanical arm module. In some embodiments, said at least one redundant and/or backup hardware is adapted to perform the same and/or similar and/or different tasks of said at least one of said modules. In some embodiments, when said at least one module cannot perform, said at least one redundant and/or backup hardware performs the task instead of said module. In some embodiments, said at least one module and said at least one redundant and/or backup hardware perform the same and/or similar and/or different tasks at the same time.

An aspect of some embodiments of the invention relates to modular pharmaceutical dispensing machines comprising at least one module and at least one redundant hardware, said at least one redundant hardware adapted to perform the same task as said at least one module, with the same configuration and/or a similar configuration and/or a different configuration of said at least one module. In some embodiments, said at least one module and said at least one redundant hardware operate concomitantly. In some embodiments, said at least one module and/or said at least one redundant hardware can be replaced with a different configuration according to the demands and/or the needs of the place where said modular pharmaceutical dispensing machine is located. In some embodiments, replacement of said at least one module or said at least one redundant hardware does not interrupt the operation of each other. In some embodiments, the configuration of said at least one module and/or said at least one redundant hardware are the same. In some embodiments, the configuration of said at least one module and/or said at least one redundant hardware are similar. In some embodiments, the configuration of said at least one module and/or said at least one redundant hardware are different. In some embodiments, the configuration of said at least one module and/or said at least one redundant hardware complement each other according to the demands and/or the needs of the place where said modular pharmaceutical dispensing machine is located.

An aspect of some embodiments of the invention relates to pharmaceutical dispensing machines comprising at least one module where said at least one module can be removed and/or replaced from said pharmaceutical dispensing machine without interrupting the functioning of said machine.

An aspect of some embodiments of the invention relates to maintaining a pharmaceutical dispensing machine comprising at least one module where the time required to remove and/or replace said at least one module is known. In some embodiments, scheduling and/or performing maintenance is done according to the scheduled activity of said pharmaceutical dispensing machine and/or said known time required to remove and/or replace said at least one module. In some embodiments, maintenance is schedule when said pharmaceutical dispensing machine is not active. In some embodiments, maintenance is schedule when said pharmaceutical dispensing machine is active and said pharmaceutical dispensing machine comprises at least one redundant hardware, adapted to perform the same task as said at least one module.

An aspect of some embodiments of the invention relates to modular pharmaceutical dispensing machines comprising at least one module and at least one redundant hardware, where said modular pharmaceutical dispensing machine comprises hardware and software adapted to perform monitoring of the performance of said at least one module and at least one redundant hardware and operate them according to said monitoring. In some embodiments, operation of said at least one module and at least one redundant hardware means activating one of them and deactivating the other. In some embodiments, operation of said at least one module and at least one redundant hardware means activating both of them concomitantly. In some embodiments, when the performance of said at least one module and/or at least one redundant hardware is not according to determined parameters, the machines sends a signal to the server and/or user notifying of the occurrence.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary Previous Pharmaceutical Dispensing Systems/Methods

Over the years, pharmacies have been a backbone in providing prescription drugs and other medications to people and have been a convenience as retail pharmacies have expanded to locating close to most residential areas. Recently, pharmacies also have been placed inside of facilities such as hospitals, physician offices, malls, nursing homes, retirement homes, assisted living facilities, and other locations to make it easier for people to get access to medications and to facilitate interaction with medical personnel. Because of the numerous types of medications stored and dispensed by pharmacies, automation within the pharmacy industry has been desirable. Accordingly, numerous developments have been made to automate the pharmacy ordering, dispensing, and storage capabilities. For example, machines have been developed to store and dispense medication responsive to security codes or other identification from medical personnel or users. Also, electronic storage and dispensing carts have been developed which are often stored on each floor of a hospital to allow the carts to electronically receive dispensing instructions from a hospital pharmacy computer. Additionally, machines have been developed to store several hundred different types of medications and to dispense the medications to medical personnel for distribution to patients.

Nevertheless, little has been done to enhance storage and distribution of medications in nursing homes, retirement homes, Alzheimer's living facilities, senior communities, assisted living facilities, and other types of long term care facilities (hereinafter collectively "long-term care facilities") which are significantly different in operation, personnel structure, and physical structure than hospitals, physician offices, and home care. Because more and more people are and will be entering these long-term care facilities and because medication costs have been rising over the years, attempting to help make pharmacies, providing services to these long term facilities, profitable can often be important in successfully operating a long-term care facility. Further, technical reliability of the pharmaceutical dispensing machines is critical for these facilities since malfunctioning of the machines can cause patients to not receive the necessary pharmaceuticals on time.

Figure 1:
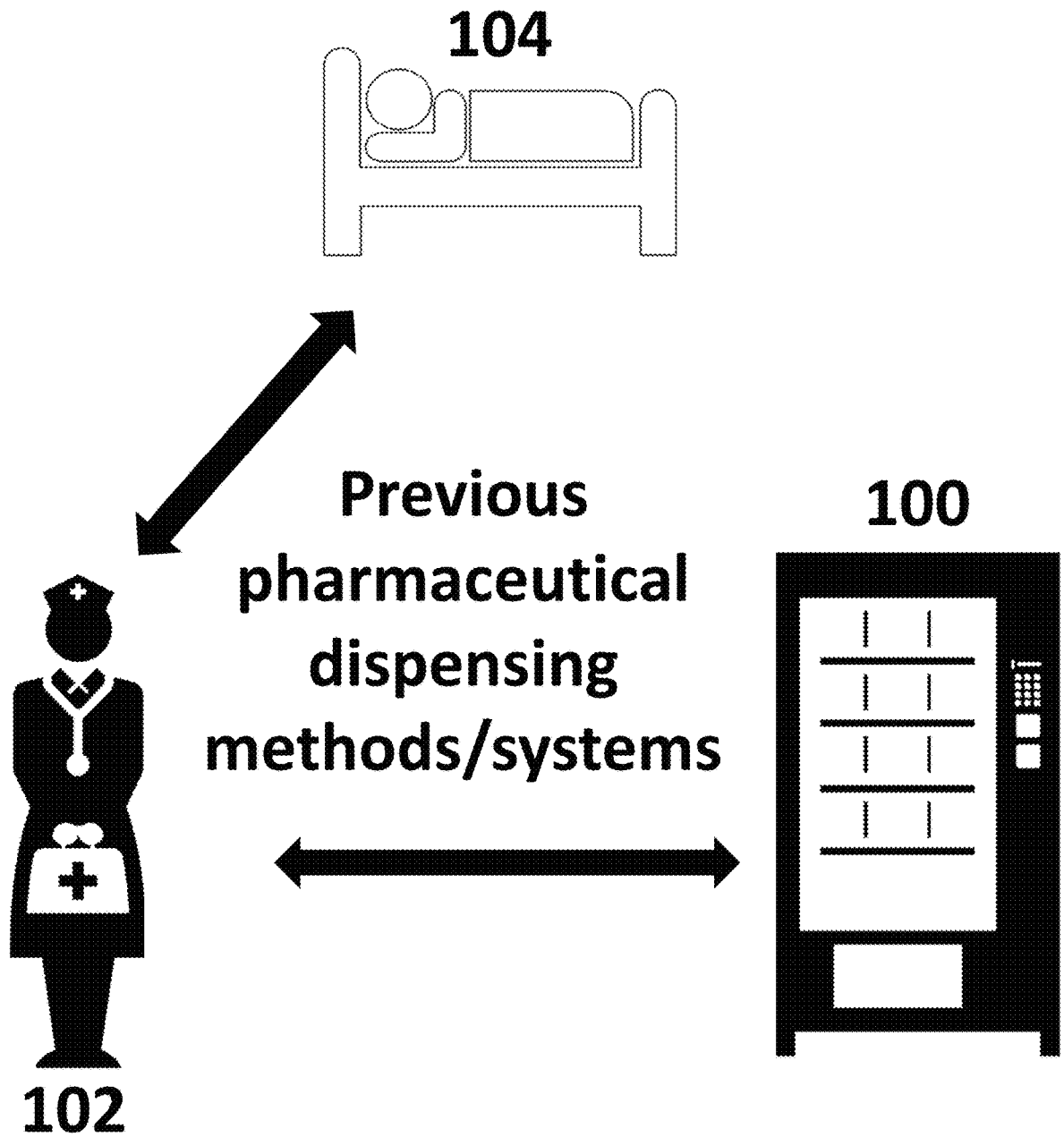
FIG. 1 is a schematic representation of exemplary previous pharmaceutical dispensing systems/methods.

Referring now to FIG. 1, showing a schematic representation of an exemplary prior art system used, for example, in a long term care facility. The system usually comprises a storage and dispensing machine 100, which is brought to the long term care facility. There, a nurse 102 collects the pharmaceuticals and brings them to the patients 104.

While this system provides a partial response to the needs of the long term care facility, it does not guarantee a reliable long-term solution. It is common, in these prior art systems, that the machine stops working due to, for example, a technical malfunction, maintenance or unscheduled refill of pharmaceuticals. In any of these scenarios, the personnel of the long term care facility is required again to deal directly with the pharmaceuticals until the machine is repaired and/or resupplied.

Exemplary Pharmaceutical Dispensing Machine According to Some Embodiments of the Invention In some embodiments, a pharmaceutical dispensing machine comprising at least one backup and/or redundant software and/or hardware is provided.

In some embodiments, the pharmaceutical dispensing machine comprises at least one module. In some embodiments, the pharmaceutical dispensing machine comprises a plurality of modules. In some embodiments, said at least one module comprises at least one backup and/or redundant hardware and/or module adapted to perform the same and/or similar and/or different functions. In some embodiments, said at least one module and said at least one backup and/or redundant hardware and/or module perform tasks at the same time.

In some embodiments, said at least one module comprises at least one unit. In some embodiments, said at least one module comprises a plurality of units. In some embodiments, said at least one unit comprises at least one backup and/or redundant hardware and/or unit adapted to perform the same and/or similar and/or different functions. In some embodiments, said at least one unit and said at least one backup and/or redundant hardware and/or unit perform tasks at the same time.

In some embodiments, said at least one unit comprises at least one element. In some embodiments, said at least one unit comprises a plurality of elements. In some embodiments, said at least one element comprises at least one backup and/or redundant hardware and/or element adapted to perform the same and/or similar and/or different functions. In some embodiments, said at least one element and said at least one backup and/or redundant hardware and/or element perform tasks at the same time.

Figure 2:
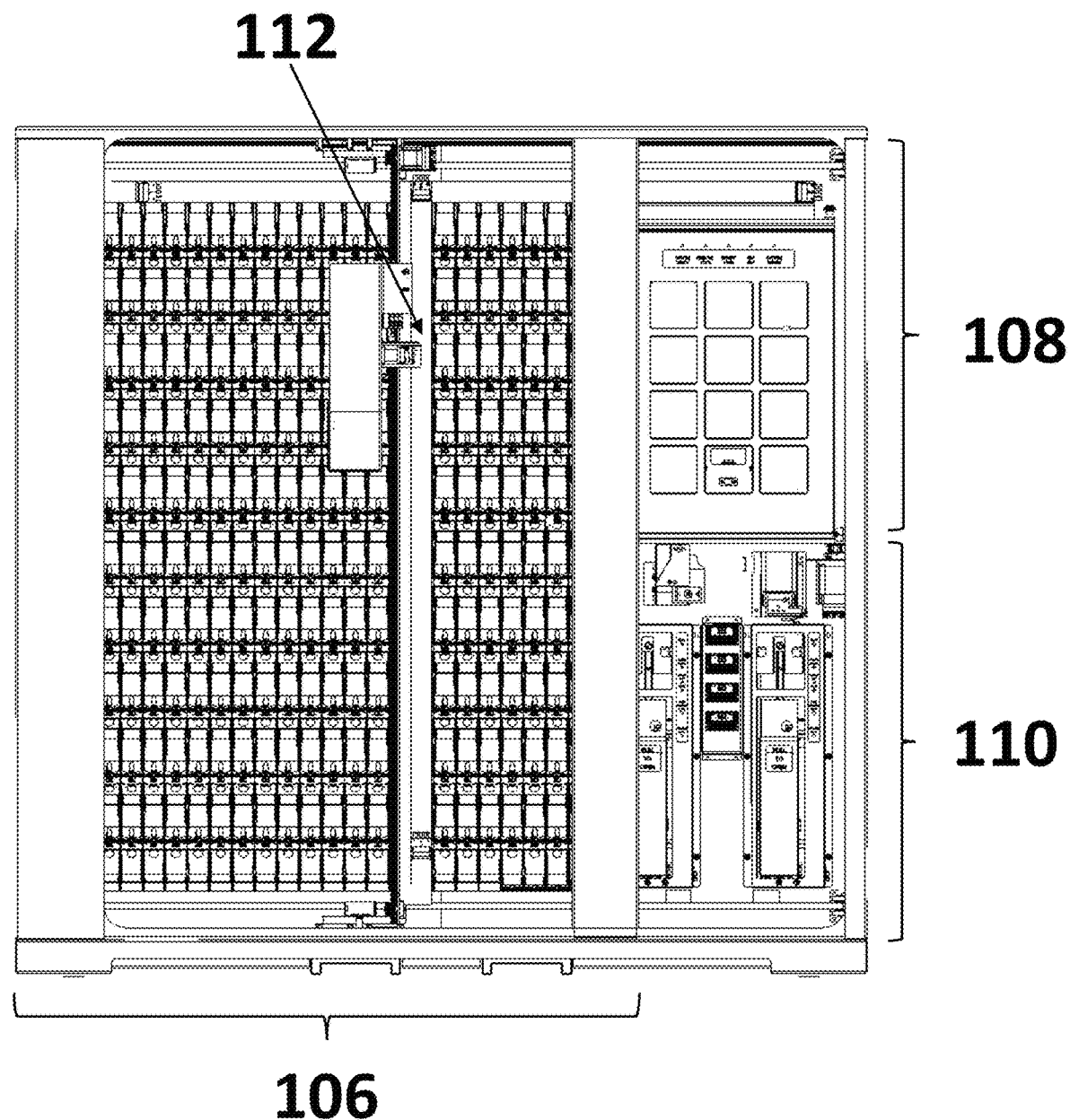
FIG. 2 is showing an exemplary pharmaceutical dispensing machine, according to some embodiments of the present invention.

Referring now to FIG. 2, showing an exemplary pharmaceutical dispensing machine according to some embodiments of the present invention. In some embodiments, the pharmaceutical dispensing machine comprises at least one module selected from the group consisting of: a pharmaceutical array module 106, a pharmaceutical tote module 108, a pharmaceutical operational modules section 110 and a mechanical arm module 112.

In some embodiments, the modules, the units and the elements, comprise at least one dedicated sensor adapted to monitor the functioning and/or the performance and/or the demands of the modules/units/elements. In some embodiments, the at least one dedicated sensor is activated remotely by a user via a dedicated server.

In some embodiments, verification on functionality of hardware, updated software, content (i.e. pharmaceuticals), consumables (i.e. envelopes) is performed on the modules, the units and the elements. In some embodiments, a user and/or a technician at the site of the pharmaceutical dispensing machine perform the verification. In some embodiments, a user and/or a technician perform the verification remotely.

Figure 3:
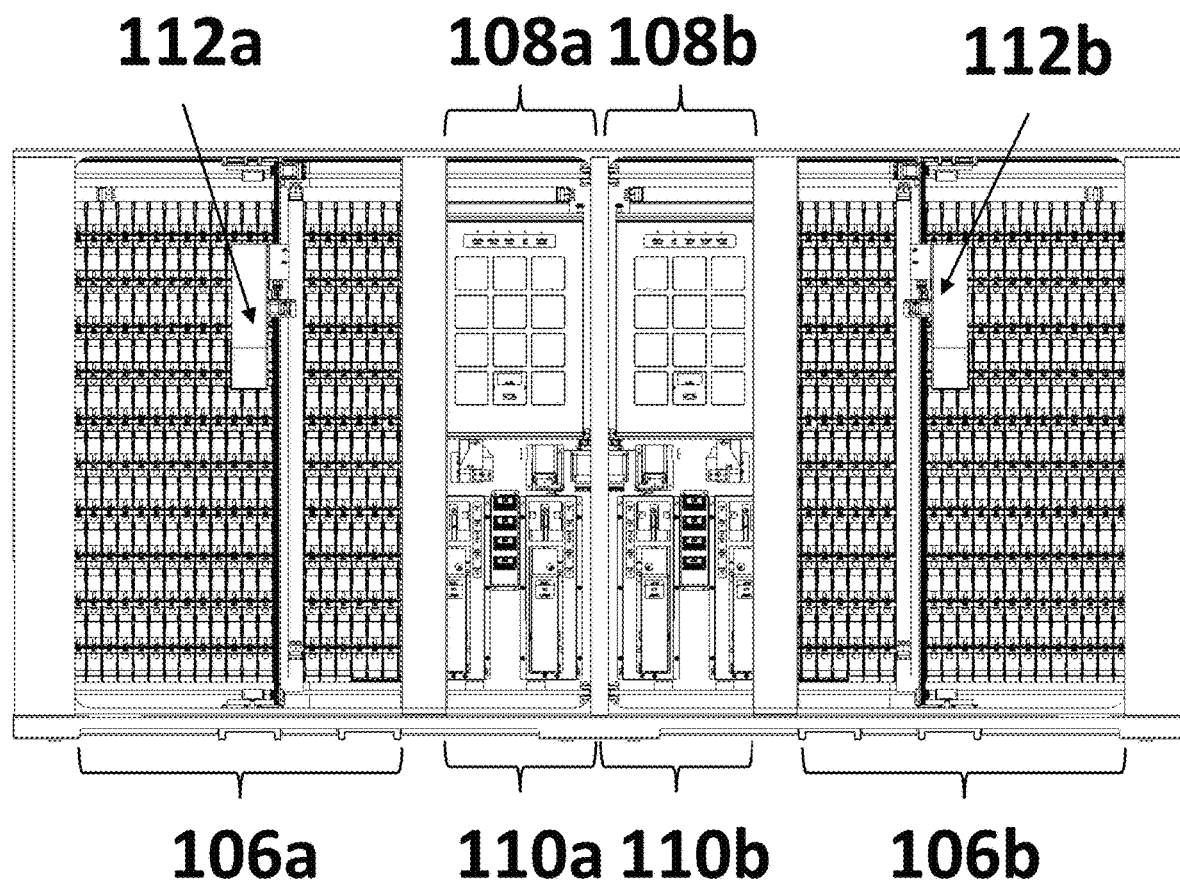
FIG. 3 is a schematic representation of a pharmaceutical dispensing machine comprising backup and/or redundant modules, according to some embodiments of the present invention.

Referring now to FIG. 3, showing a schematic representation of an exemplary pharmaceutical dispensing machine comprising backup and/or redundant hardware and/or modules. In some embodiments, the pharmaceutical dispensing machine comprising backup and/or redundant hardware and/or modules comprises at least two pharmaceutical array modules (106a and 106b), at least two pharmaceutical tote modules (108a and 108b), at least two pharmaceutical control modules (110a and 110b) and at least two mechanical arm modules (112a and 112b).

In some embodiments, only one module is operated while the backup and/or redundant hardware and/or module is inactive. In some embodiments, both the main module and the backup and/or redundant hardware and/or module are operated simultaneously.

In some embodiments, the modules, either main module or backup and/or redundant hardware and/or module can be operated independently to other hardware and/or modules. For example, in the pharmaceutical dispensing machine shown in FIG. 3, the two pharmaceutical array modules (106a and 106b) can be operated while only one pharmaceutical tote module (108a or 108b) is operated. Similarly, the two pharmaceutical array modules (106a and 106b) and the two pharmaceutical tote modules (108a and 108b) are operated while only one pharmaceutical operational module section (110a or 110b) is operated.

Figure 4:
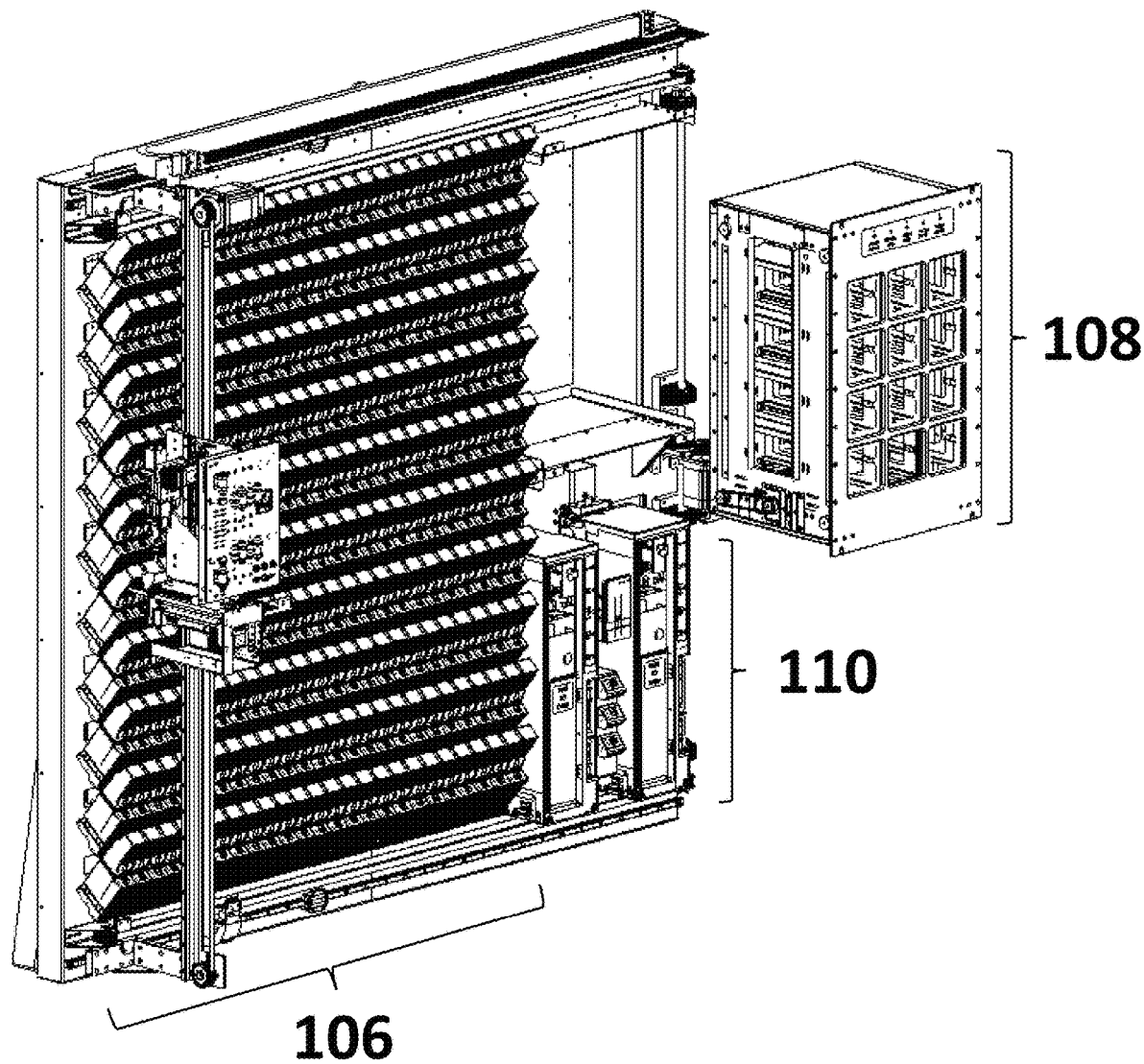
FIG. 4 is a schematic representation of a pharmaceutical tote module, according to some embodiments of the present invention.

In some embodiments, the modules are designed to be an independent part of the pharmaceutical dispensing machine. For example, the pharmaceutical tote module 108 can be disconnected (dismounted) from the frame of the pharmaceutical dispensing machine completely, without affecting the rest of the modules. Referring now to FIG. 4, showing a schematic representation of a pharmaceutical tote module 108 being disconnected (dismounted) from the frame of the pharmaceutical dispensing machine as example of dismounting a module. In some embodiments, each module (106, 108, 110 and 112) can be extracted from the frame of the pharmaceutical dispensing machine. In some embodiments, each module (106, 108, 110 and 112) can be extracted from the frame of the pharmaceutical dispensing machine without the need to stop the operation of the machine.

In some embodiments, this configuration is potentially advantageous during repairs and/or maintenance. In some embodiments, the time required to bring the pharmaceutical dispensing machine to normal functioning is very short (i.e. minutes). In some embodiments, the technician can pull out a module and then insert a new one at its place. In some embodiments, the time to replace either a module, a unit or an element from said pharmaceutical dispensing device is from about 1 minute to about 10 minutes. Optionally from about 5 minutes to about 30 minutes. Optionally from about 10 minutes to about 60 minutes.

Exemplary Pharmaceutical Array Module 106

Figure 5:
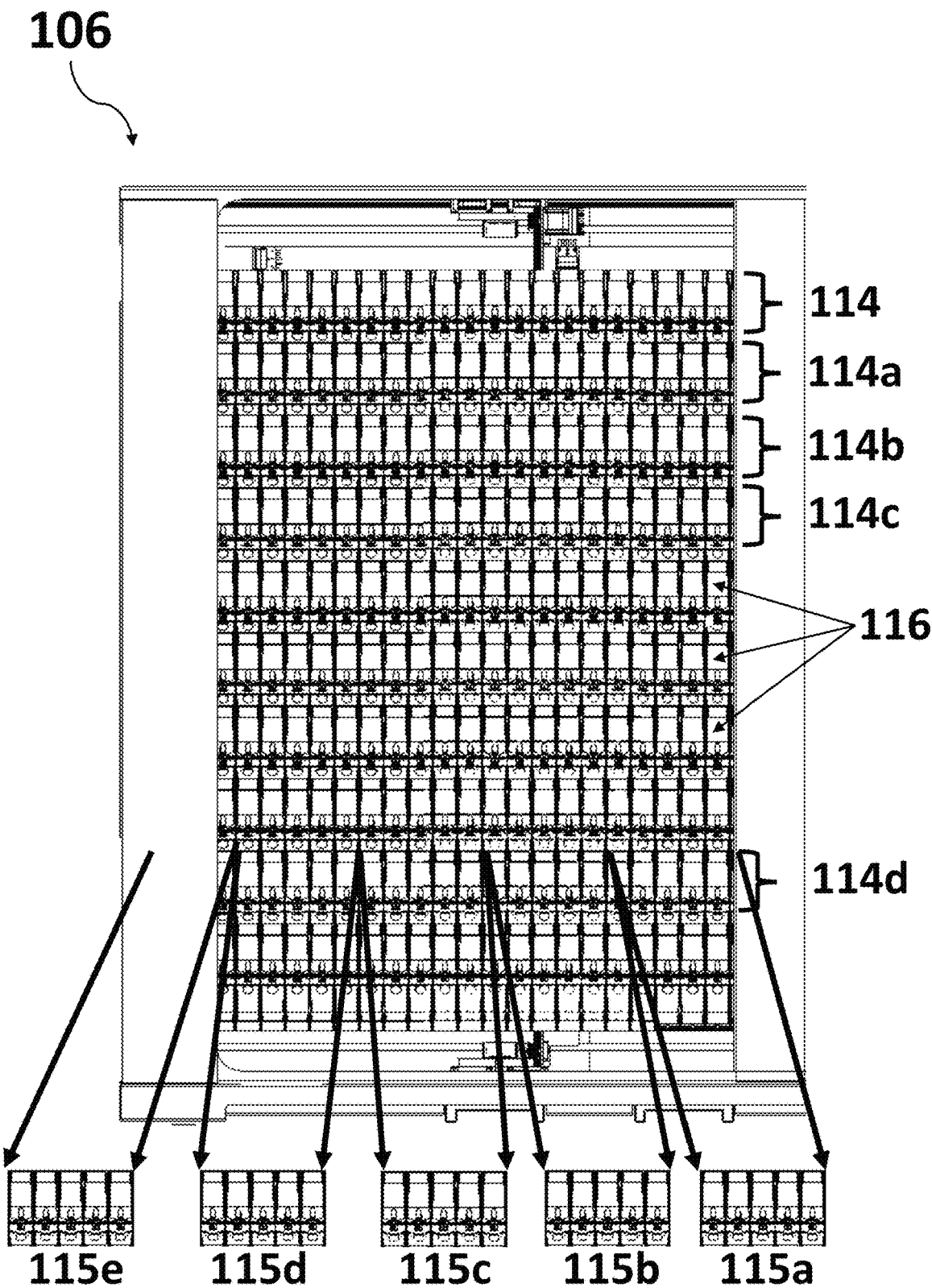
FIG. 5 is a schematic representation of a pharmaceutical array module, according to some embodiments of the present invention.

Referring now to FIG. 5, showing a schematic representation of a pharmaceutical array module 106. In some embodiments, the pharmaceutical array module 106 is responsible for the storage of a variety of pharmaceuticals. In some embodiments, the pharmaceutical array module 106 comprises a plurality of drug units 114, which each further comprise a plurality of drug elements 116, in which pharmaceuticals are stored.

In some embodiments, the number of drug units 114 in the pharmaceutical array module 106 is from about 1 to about 500. Optionally, the number of drug units 114 in the pharmaceutical array module 106 is from about 4 to about 300. Optionally, the number of drug units 114 in the pharmaceutical array module 106 is from about 10 to about 200. In some embodiments, each drug unit comprises a backup and/or redundant drug unit adapted to include the same drug elements 116.

In some embodiments, each drug unit 114 is designed to be an independent part of the pharmaceutical array module 106. For example, the drug unit 114a can be disconnected (dismounted) from the frame of the pharmaceutical array module 106, completely, without affecting, for example, the correct functioning of the drug units 114b and/or 114c. In some embodiments, a drug unit 114 is adapted to include a specific number of drug elements 116 within. In some embodiments, the number of drug elements within a drug unit is from about 2 to about 200. Optionally, is from about 5 to about 150. Optionally, is from about 10 to 100. In some embodiments, each row of drug unit 114 comprises a plurality of drug subunits 115a-e arranged one after the other, as shown for example, in row drug unit 114d.

In some embodiments, a drug unit comprises a backup and/or redundant drug unit adapted to perform the same function. In some embodiments, a drug subunit comprises a backup and/or redundant drug subunit adapted to perform the same function.

Figure 6:
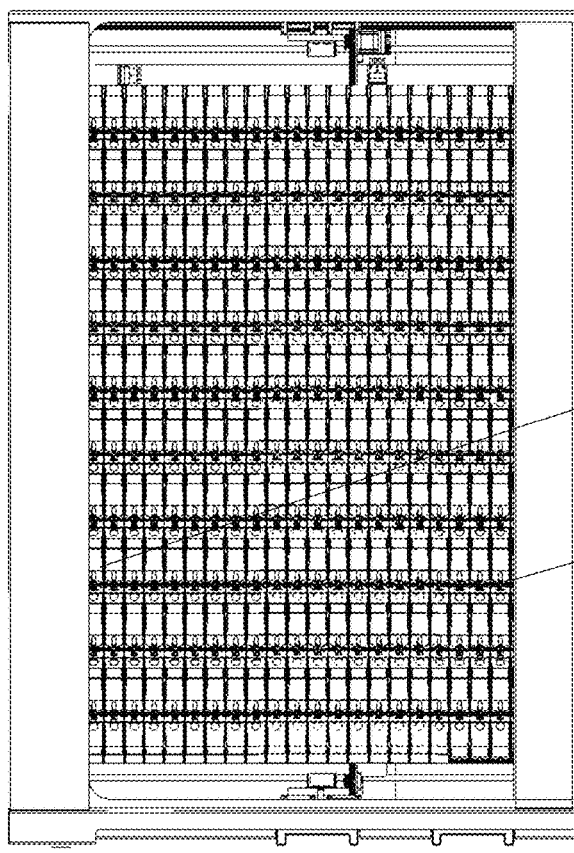
FIG. 6 is a schematic representation of a drug unit being disconnected (dismounted) from the frame of the pharmaceutical array module, according to some embodiments of the present invention.
Figure 6:
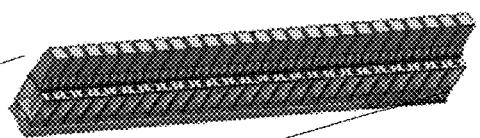

Referring now to FIG. 6, showing a schematic representation of a drug unit 114 being disconnected (dismounted) from the frame of the pharmaceutical array module 106 as example of dismounting a drug unit.

In some embodiments, this configuration is potentially advantageous during repairs and/or maintenance. In some embodiments, the time required to bring the pharmaceutical dispensing machine to normal functioning is very short (i.e. minutes). In some embodiments, the technician can pull out a unit and then insert a new one at its place. In some embodiments, during repairs and/or maintenance a backup and/or redundant drug unit and/or drug subunit performs the function of the drug unit and/or drug subunit that is being repaired and/or maintained.

Exemplary Drug Unit 114/Drug Subunit 115

Figure 7:
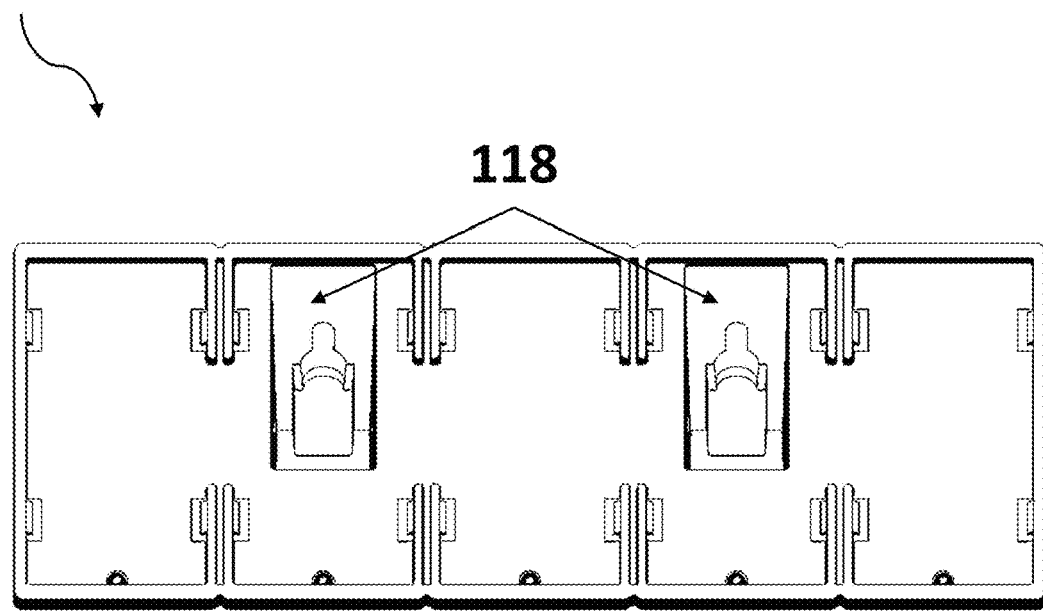
FIG. 7 is an exemplary drug unit and/or drug subunit with five spaces for five drug elements, according to some embodiments of the present invention.
Figure 7:
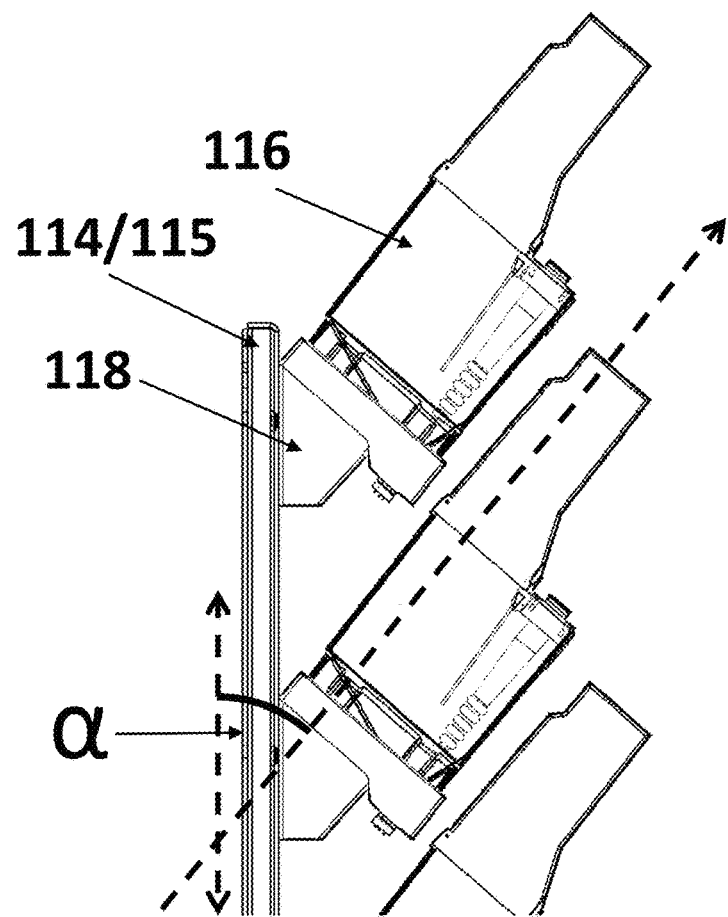

Referring now to FIG. 7, showing an exemplary drug unit 114 and/or drug subunit 115 with five spaces for five drug elements 116. In some embodiments, the drug units 114/subunits 115 are adapted to include a plurality of drug elements 116 within. In some embodiments, the number of drug elements within a drug subunit is from about 2 to about 20. Optionally, is from about 5 to about 15. Optionally, is from about 7 to 10. In some embodiments, the drug units 114/subunits 115 comprise an adapter 118 configured to receive and lock in place a drug element 116. In some embodiments, pharmaceuticals are stored in the drug elements. In some embodiments, each drug element stores a different pharmaceutical. Optionally, several drug elements store the same kind of pharmaceuticals.

In some embodiments, the drug units 114/subunits 115 can have a horizontal orientation with respect to the pharmaceutical array module 106. In some embodiments, the drug units 114/subunits 115 can have a vertical orientation with respect to the pharmaceutical array module 106.

In some embodiments, the adapters 118 are configured to provide the drug elements 116 with an angle α in relation to the wall of the drug unit 114/subunit 115 on which they are connected. In some embodiments, the angle α is from about 10 degrees to about 90 degrees. Optionally, the angle α is from about 20 degrees to about 60 degrees. Optionally, the angle α is from about 30 degrees to about 50 degrees. Optionally, the angle α is 30 degrees or 45 degrees or 60 degrees.

In some embodiments, each drug element comprises a backup and/or redundant drug element including the same type of pharmaceuticals.

Figure 8:
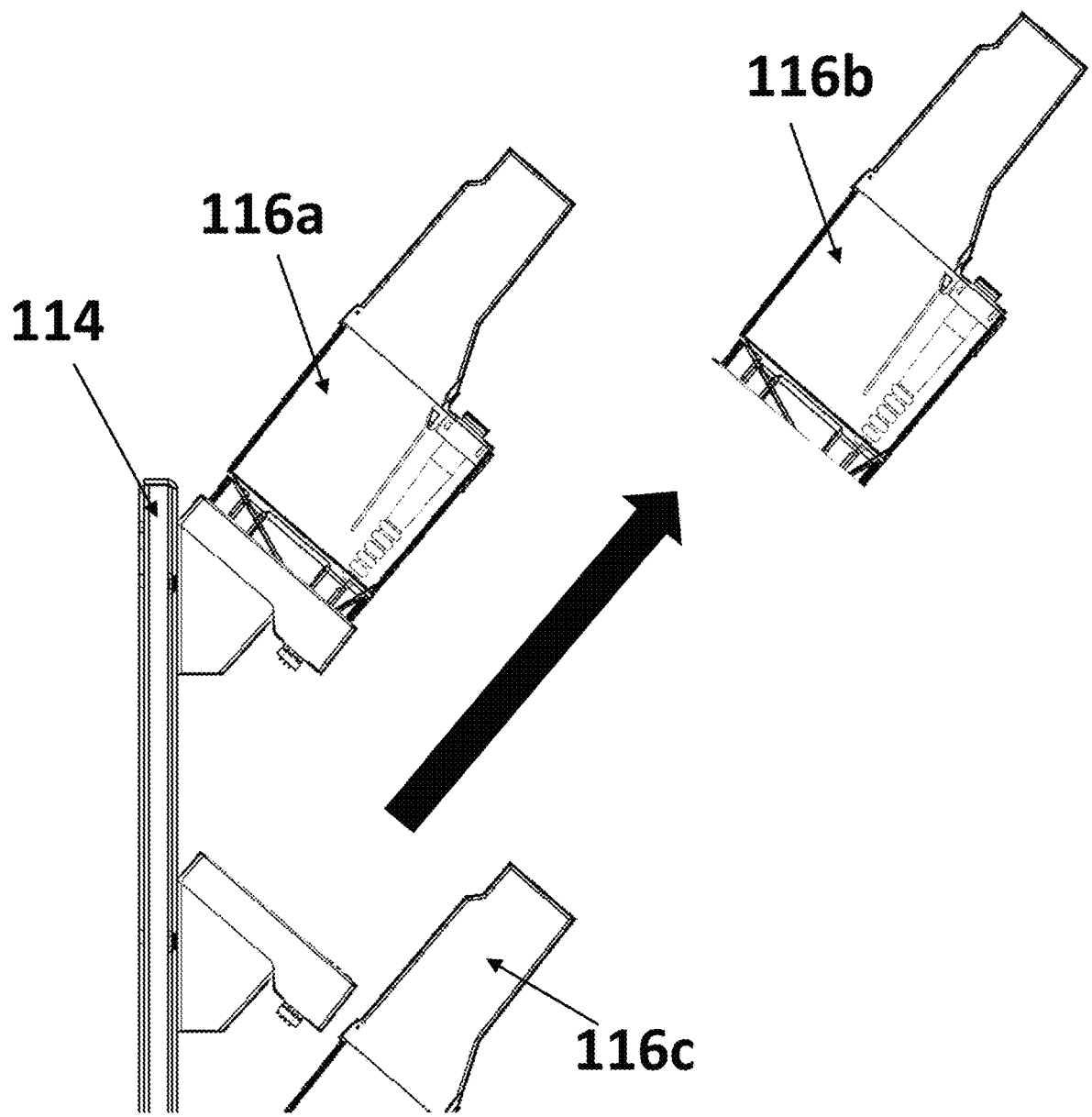
FIG. 8 is a schematic representation of a drug element being disconnected (dismounted) from drug unit, according to some embodiments of the present invention.

In some embodiments, each drug element 116 is designed to be an independent part of the drug unit 114/subunit 115. Referring now to FIG. 8, showing a schematic representation of a drug element 116b being disconnected (dismounted) from drug unit 114 as example of dismounting a drug element. For example, the drug element 116b can be disconnected (dismounted) from the frame of the drug unit 114, completely, without affecting, for example, the correct functioning of the drug elements 116a and/or 116c.

In some embodiments, this configuration is potentially advantageous during repairs and/or maintenance. In some embodiments, the time required to bring the pharmaceutical dispensing machine to normal functioning is very short (i.e. minutes). In some embodiments, the technician can pull out a unit and then insert a new one at its place. In some embodiments, during repairs and/or maintenance a backup and/or redundant drug element performs the function of the drug element that is being repaired and/or maintained.

Exemplary Drug Element 116

Figure 9:
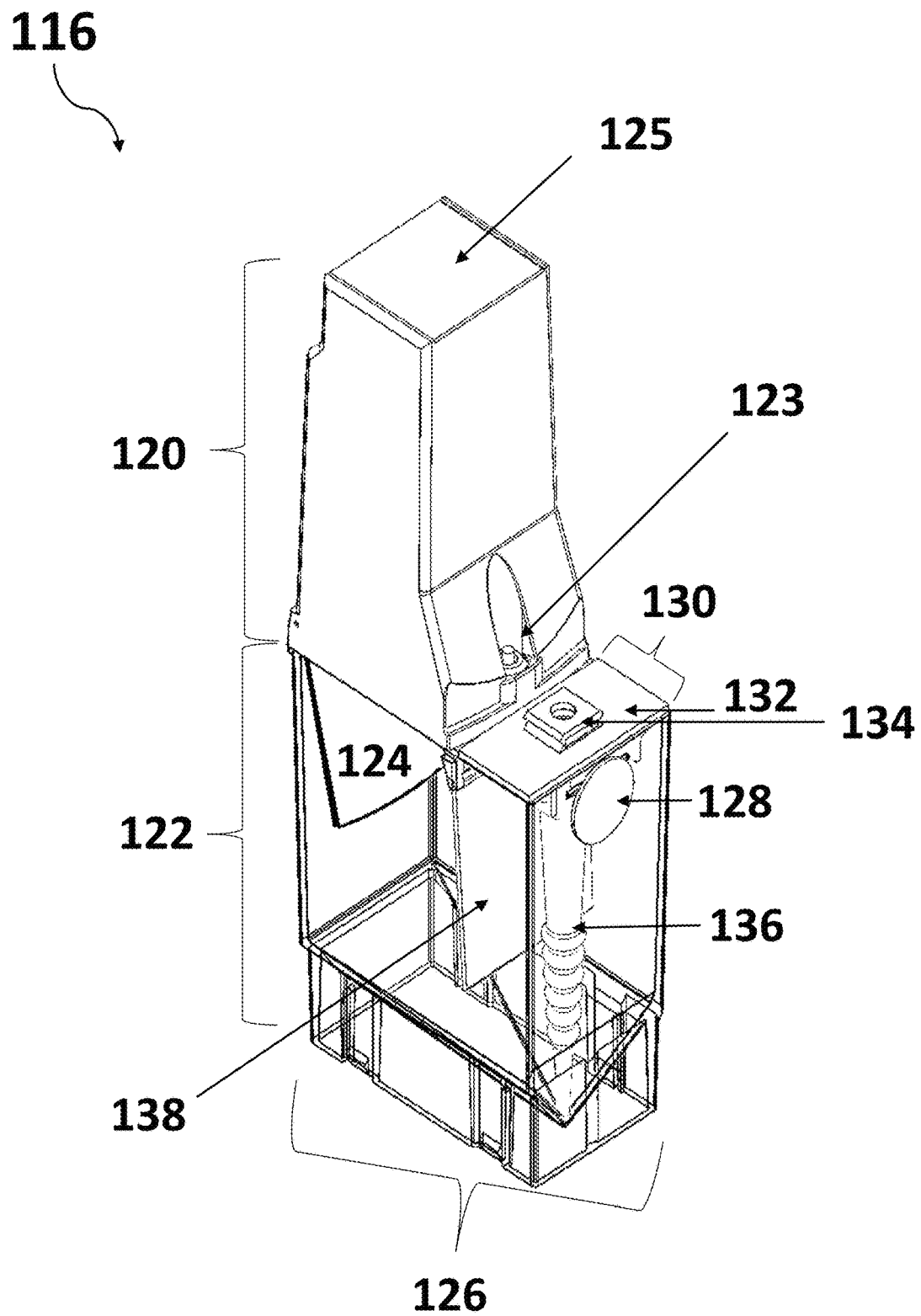
FIG. 9 is a schematic representation of a drug element, according to some embodiments of the present invention.

Referring now to FIG. 9, showing a schematic representation of a drug element 116. In some embodiments, each drug element 116 comprises two main parts: a cartridge 120 and a container 122. In some embodiments, the cartridge 120 and the container 122 can be separated from each other. In some embodiments, the cartridge 120 is filled with single pharmaceutical pills. In some embodiments, after the cartridge 120 is connected to the container 122, at the first use, a component in the mechanical arm module 112, engages button 123, which releases a flap 124, located at the bottom of the cartridge 120, thereby releasing the pharmaceutical pills into the container 122. In some embodiments, the pill located in the cartridge 120 are released only when pills located in the container 122 are finished. In some embodiments, the pills located in the cartridge 120 are used as backup pills for the pills located in the container 122. In some embodiments, the cartridge comprises a tag 125 (or a barcode or a qcode) at the top, comprising the relevant information regarding the pharmaceutical inside the cartridge. In some embodiments, the container 122 comprises a base 126 configured to interconnect with the adapter 118 of the drug unit 114. In some embodiments, the container 122 comprises an electronic tag 128, which includes the information related to the pharmaceuticals in the drug element 116. In some embodiments, the electronic tag 128 is an RFID tag. Optionally, the electronic tag is a data dot, a barcode or qcode. In some embodiments, the container 122 comprises a probe assembly 130 comprising a cap 132 with an adaptor 134 configured to interconnect with a part of the mechanical arm module 112 and a probe 136 adapted to engage a single pharmaceutical pill (see below pill engagement mechanism 146). In some embodiments, the container 122 optionally comprises a pill dam 138 adapted to partially hold and separate the single pharmaceutical pills from the zone of the straw 136 of the probe 130. In some embodiments, this configuration is potentially advantageous to facilitate the engagement with a single pharmaceutical pill.

In some embodiments, the cartridge 120 and/or the container 122 can be replaced without discarding the other.

In some embodiments, the machine comprises a plurality of spare probes in case a probe wears out and/or malfunctions. In some embodiments, a variety of designs of probes are used in the machine, for example, adapted to engage different types of pills. For example, the distal end of the probe, which engages the pills, can be designed with a circular geometry adapted to engage circular pills. Optionally, bigger probes are adapted to engage bigger pills.

In some embodiments, the drug elements may comprise different number of pills, different size of pills and/or different weight of pills.

Exemplary Mechanical Arm Module 112

Figure 10:
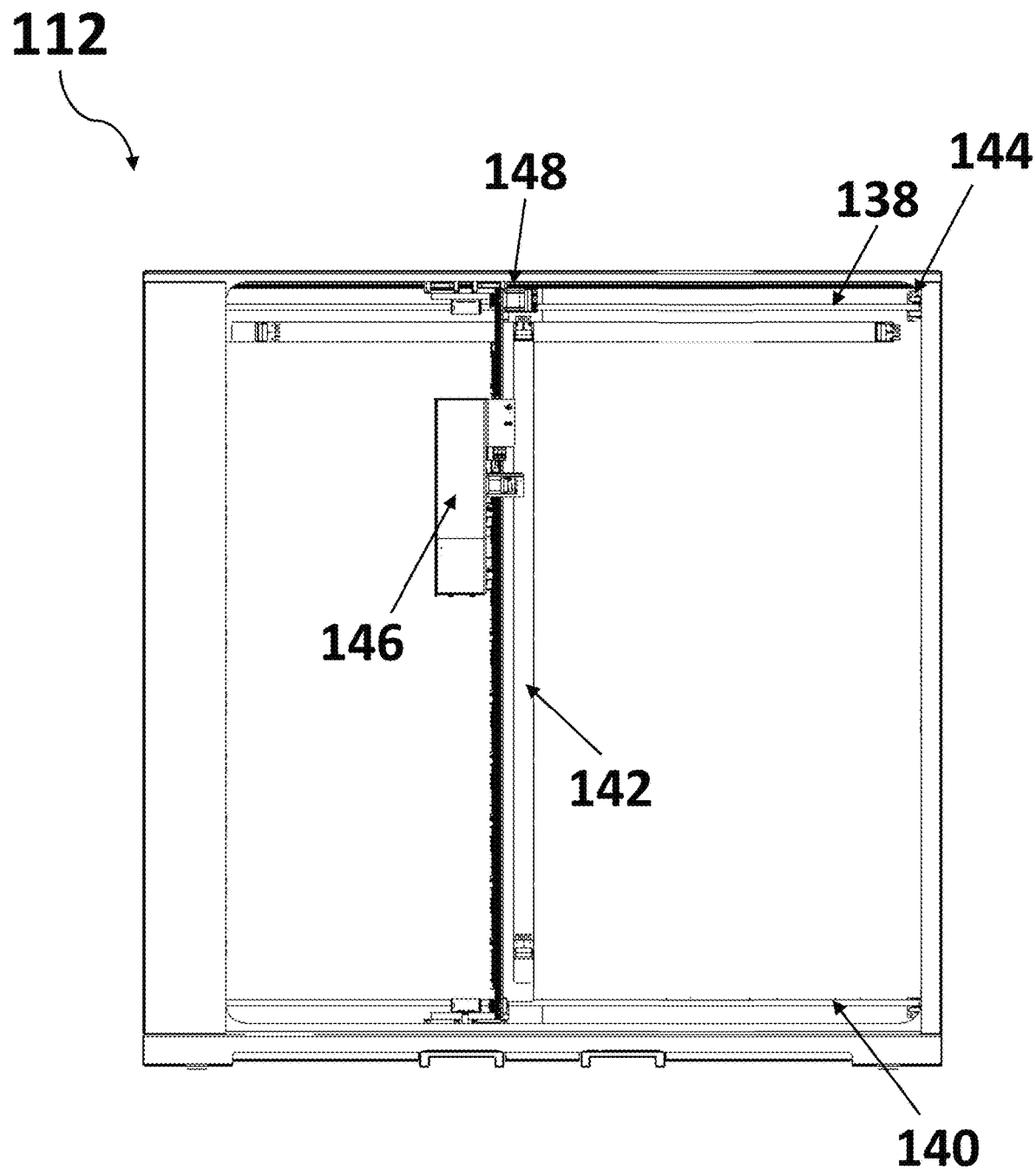
FIG. 10 is a schematic representation of a mechanical arm module, according to some embodiments of the present invention.

Referring now to FIG. 10 showing a schematic representation of a mechanical arm module 112. In some embodiments, the mechanical arm module 112 comprises two horizontal rails (138 and 140) on which a vertical axle 142 runs horizontally (right and left, left and right) by means of a motor 144 (located, for example, on the right corner of the machine in FIG. 10). In some embodiments, the vertical axle 142 moves horizontally as much as the length of the two horizontal axles (138 and 140). In some embodiments, the mechanical arm module 112 further comprises a pharmaceutical pill engagement mechanism 146 that runs vertically (up and down, down and up) on the vertical axle 142 by means of a motor 148. In some embodiments, the pharmaceutical pill engagement mechanism 146 moves vertically as much as the length of the vertical axle 142.

In some embodiments, the mechanical arm module 112 can be disconnected (dismounted) from the frame of the pharmaceutical dispensing machine without the need to dismount and/or disassemble the other modules (106, 108 and 110). Optionally, only one of the two rails is used 138 or 140. In these cases, the left right motion mechanism that provides the motion is either hanging from the top rail 138 or standing from the bottom 140.

Exemplary Pill Engagement Mechanism 146

Figure 11:
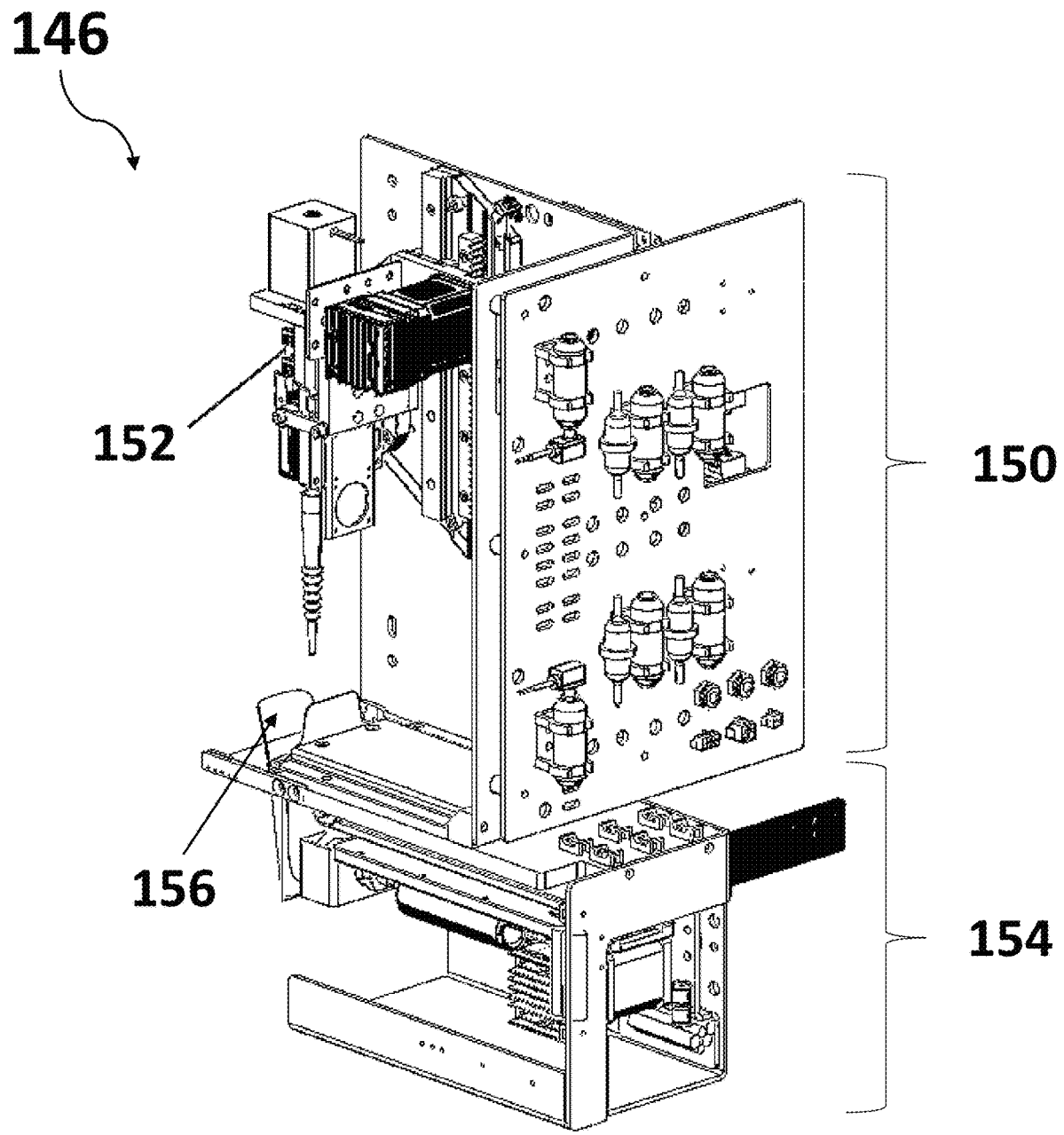
FIG. 11 is a schematic representation of the internal mechanism of the pill engagement mechanism, according to some embodiments of the present invention.

Referring now to FIG. 11, showing a schematic representation of the internal mechanism of the pill engagement mechanism 146.

In some embodiments, the pill engagement mechanism 146 utilizes a vacuum system to engage a single pharmaceutical pill. In some embodiments, the pill engagement mechanism 146 comprises a vacuum mechanism 150, which includes all necessary electronics and pumps. In some embodiments, the vacuum mechanism 150 comprises a probe engagement tool 152 adapted to engage the probe 130 in the container 122. In some embodiments, the pill engagement mechanism 146 optionally comprises an envelope engaging tool 154 adapted to hold and handle an envelope 156 into which the pharmaceuticals will be inserted.

Figure 12:
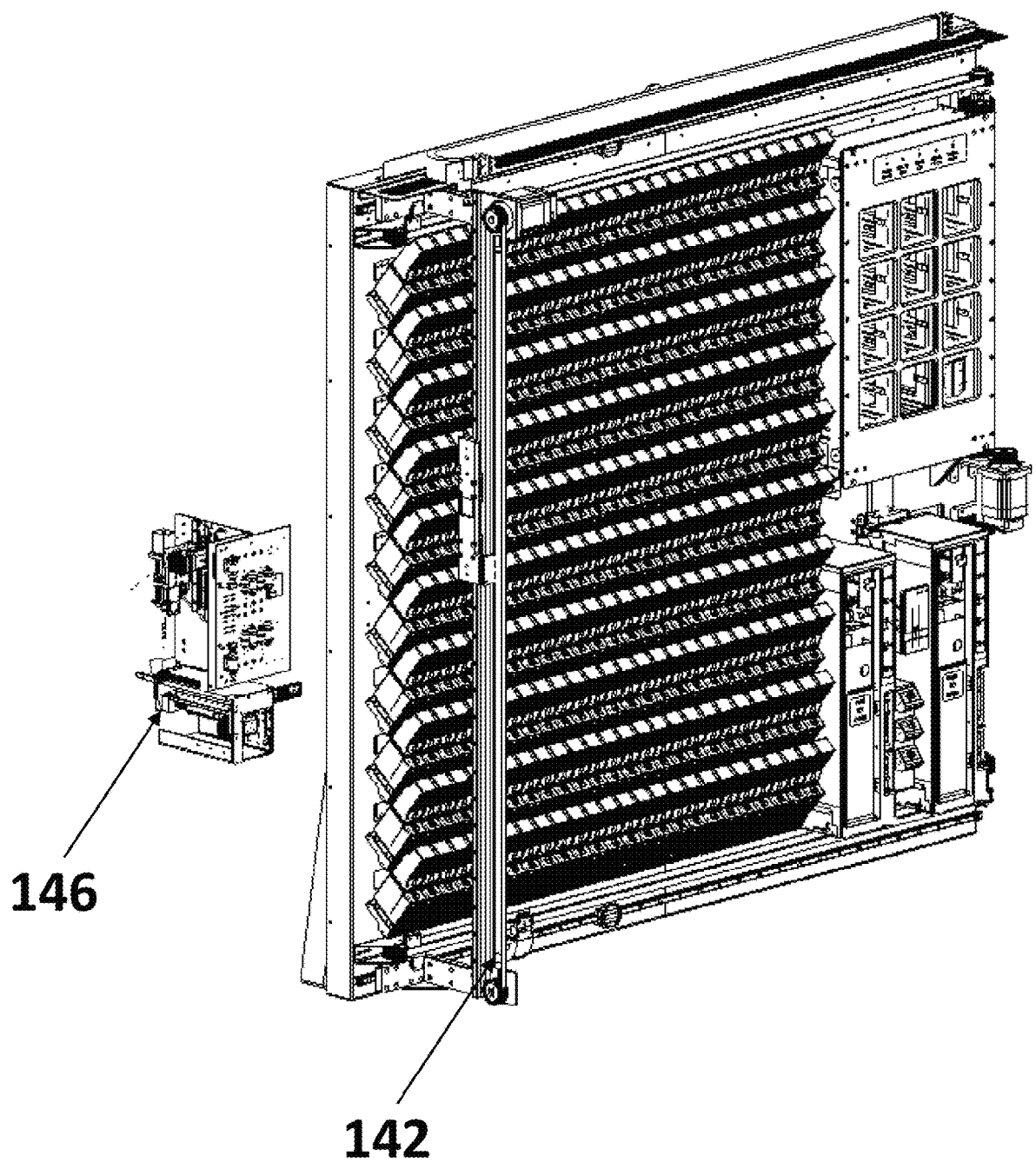
FIG. 12 is schematic representation of a pill engagement mechanism being disconnected (dismounted) from the vertical axle, according to some embodiments of the present invention.

Referring now to FIG. 12 showing a schematic representation of a pill engagement mechanism 146 being disconnected (dismounted) from the vertical axle 142. In some embodiments, the engagement mechanism 146 can be disconnected (dismounted) from the vertical axle 142 easily and without the need to disconnect any other part of the machine. In some embodiments, this configuration is potentially advantageous during repairs and/or maintenance.

Exemplary Pharmaceutical Tote Module 108

Figure 13:
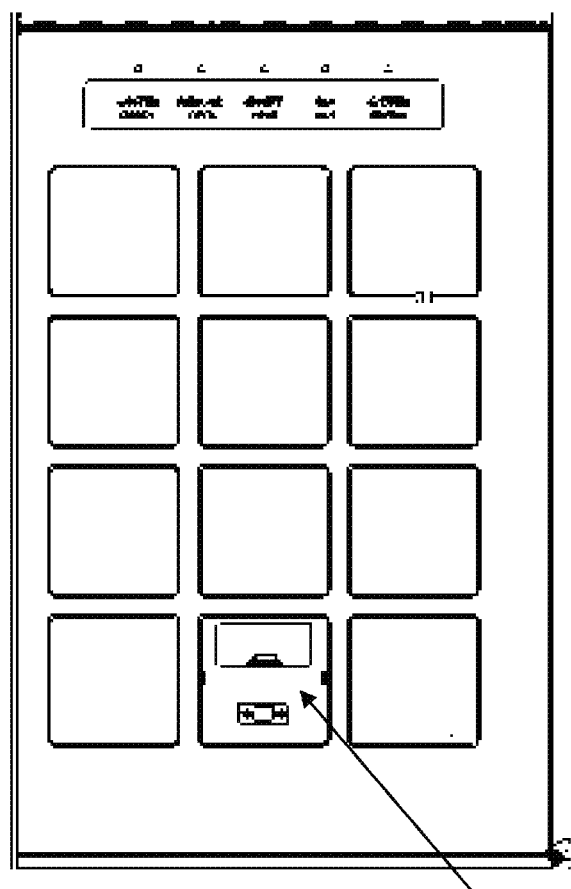
FIG. 13 is a schematic representation of a pharmaceutical tote module, according to some embodiments of the present invention.

Referring now to FIG. 13, showing a schematic representation of a pharmaceutical tote module 108. In some embodiments, after the envelopes are marked, filled with pharmaceuticals, closed, crimped and ready to be dispensed, they are inserted in trays 158 located in the pharmaceutical tote module 108. In some embodiments, the trays 158 are then picked up by the personnel of the facility and dispensed to the patients. In some embodiments, the number of trays 158 in the pharmaceutical tote module 108 is from about 1 to about 50. Optionally, the number of trays 158 in the pharmaceutical tote module 108 is from about 4 to about 40. Optionally, the number of trays 158 in the pharmaceutical tote module 108 is from about 6 to about 30. Optionally, the number of trays 158 in the pharmaceutical tote module 108 is from about 12 to about 20.

Figure 14:
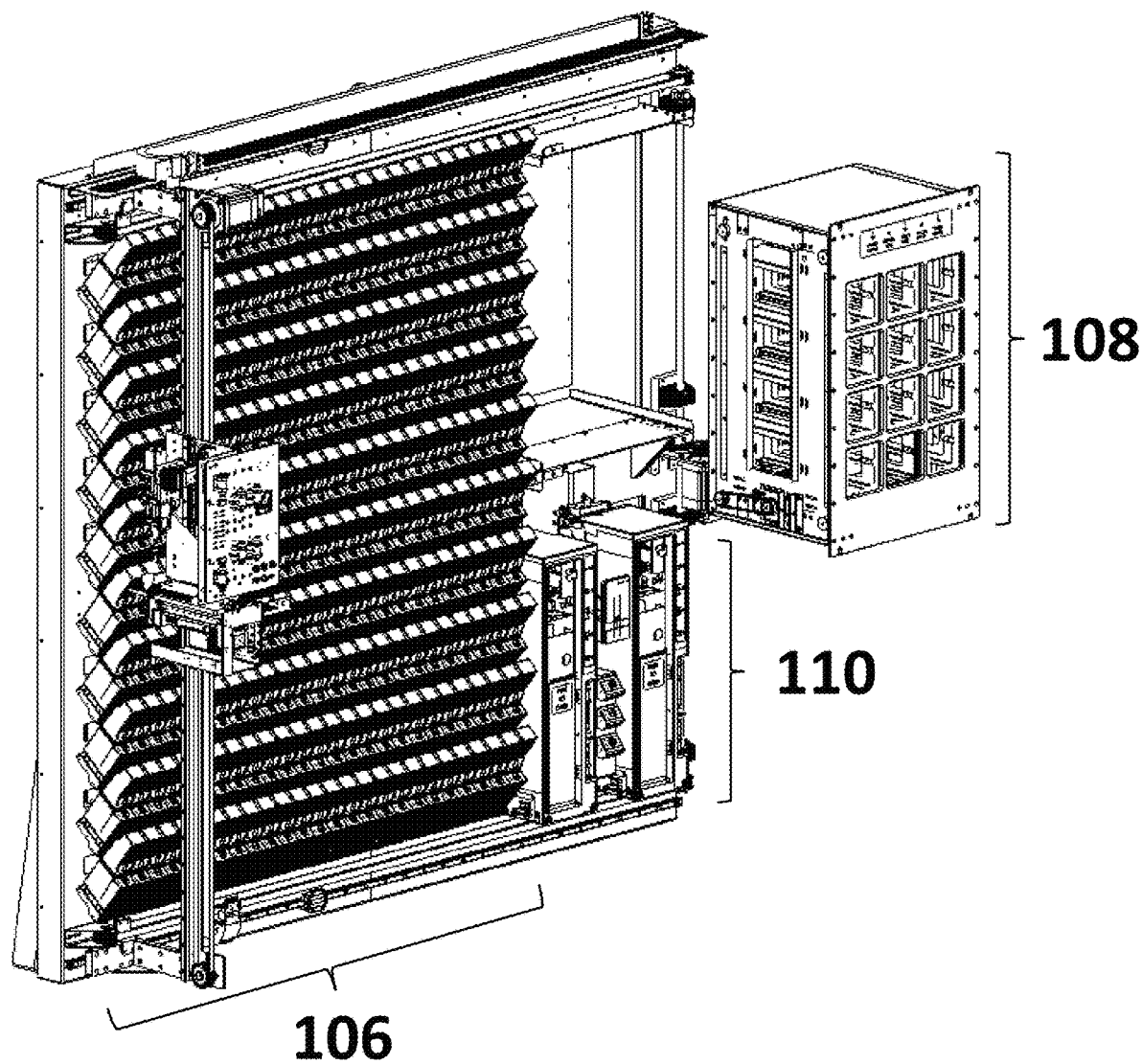
FIG. 14 is a schematic representation of a pharmaceutical tote module being disconnected (dismounted) from the frame of the pharmaceutical dispensing machine, according to some embodiments of the present invention.

Referring now to FIG. 14, showing a schematic representation of a pharmaceutical tote module 108 being disconnected (dismounted) from the frame of the pharmaceutical dispensing machine as example of dismounting a module. In some embodiments, the pharmaceutical tote module 108 can be extracted from the frame of the pharmaceutical dispensing machine without the need to dismount and/or disassemble the other modules (106, 110 and 112).

In some embodiments, this configuration is potentially advantageous during repairs and/or maintenance. In some embodiments, the time required to bring the pharmaceutical dispensing machine to normal functioning is very short (i.e. minutes). In some embodiments, the technician can pull out a module and then insert a new one at its place.

Exemplary Pharmaceutical Operational Modules Section 110

Figure 15:
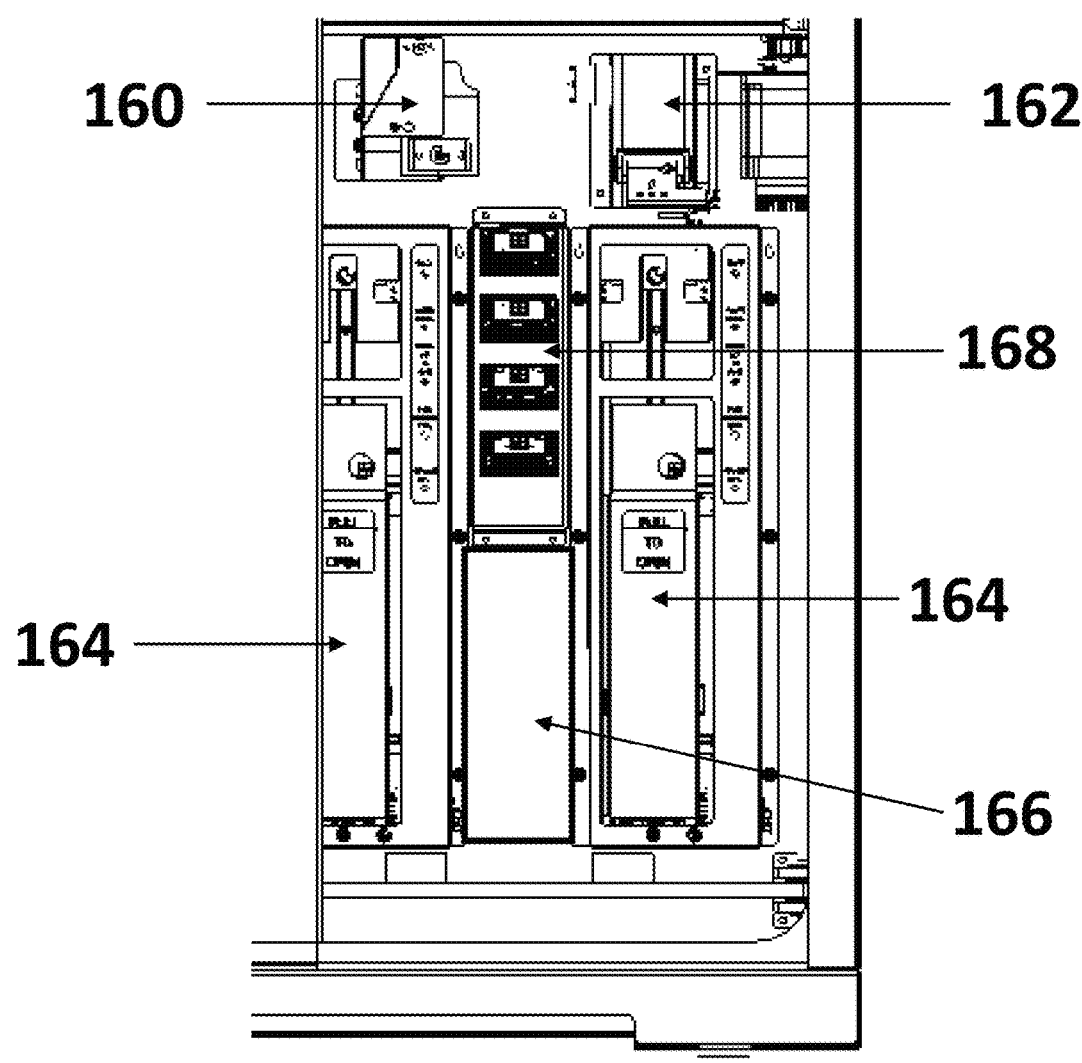
FIG. 15 is a schematic representation of an exemplary pharmaceutical operational modules section, according to some embodiments of the present invention.

In some embodiments, the pharmaceutical operational modules section 110 comprises a plurality of modules, each one responsible for a different operational aspect of the preparation and/or dispensing of the pharmaceuticals. Referring now to FIG. 15, showing a schematic representation of an exemplary pharmaceutical operational modules section 110. In some embodiments, the pharmaceutical operational modules section 110 comprises, for example, a printer module 160, a crimper module 162, at least one envelope module 164 (in this example two are shown) and a control module 166. Optionally, other techniques can be used in the different modules, for example a stapler or gluing instead of crimping. Optionally, in the pharmaceutical operational modules section 110, spare consumable parts can be stored in order for the machine to use them when necessary. For example, in FIG. 15, a plurality of probes 168 in a probe station, are shown.

In some embodiments, each of the modules located in the pharmaceutical operational modules section 110 can be disconnected (dismounted) from the frame of the pharmaceutical operational modules section 110, without affecting the operation of the rest of the modules (i.e. 160, 162, etc.). Referring now to FIGS. 16*a-c*, showing three schematic representations of disconnected parts from the pharmaceutical operational modules section 110. FIG. 16*a* shows the envelope modules 164 being disconnected (dismounted) from the pharmaceutical operational modules section 110. FIG. 16*b* shows the printer module 160 being disconnected (dismounted) from the pharmaceutical operational modules section 110. FIG. 16*c* shows the crimper module 162 being disconnected (dismounted) from the pharmaceutical operational modules section 110. In some embodiments, other backup consumables found are: ink for the printer, staples for the stapler, more envelopes, and other. In some embodiments, the personnel of the facility can replace the consumables of the modules.

Exemplary Printer Module 160

In some embodiments, the printer module 160 is responsible for printing on the envelopes 156. An exemplary printer module can be seen, for example, in FIG. 17*b*.

Exemplary Crimper Module 162

In some embodiments, the crimper module 162 is responsible for closing the envelopes 156 after the pharmaceutical have being inserted in them. An exemplary crimper module can be seen, for example, in FIG. 17*c*.

Exemplary Envelope Module 164

In some embodiments, the envelope module 164 is responsible for storing and preparing the envelopes 156 before use. An exemplary envelope module can be seen, for example, in FIG. 17*a*.

Exemplary Control Module 166

In some embodiments, the control module 166 is responsible, for example, for controlling the packaging and dispensing operations (i.e. control of the other modules), communicate with external regional or central server and perform routinely self-diagnostic test to ensure the continuous operation of the pharmaceutical dispensing machine.

Exemplary Different Configurations of the Pharmaceutical Dispensing Machine

In some embodiments, due to the modular nature of the pharmaceutical dispensing machine, a plurality of configurations are achieved. Referring now to FIGS. 18*a-c*, showing schematic representations of exemplary configurations of the pharmaceutical dispensing machine. FIG. 18a shows a schematic representation of a pharmaceutical dispensing machine where the pharmaceutical array module 106 is located on the upper side of the machine while the pharmaceutical tote module 108 and the pharmaceutical operational modules section 110, are located at the bottom. The mechanical arm module 112 is adapted to reach all necessary parts of the machine due to a modified pill engagement mechanism 146. FIG. 18b shows a schematic representation of a pharmaceutical dispensing machine where the pharmaceutical array module 106 is divided in two sections, one inside the machine and the other on the door of the machine. The pharmaceutical tote module 108 and the pharmaceutical operational modules section 110, are located at the side of the machine, as previously shown. The mechanical arm module 112 is adapted to reach both sides of the pharmaceutical array module 106 due to a modified pill engagement mechanism 146, which is enabled to rotate on its axis therefore reaching both sides of the pharmaceutical array module 106. Alternatively, two mechanical arms modules (heads) may be used, for example, one facing the back and the other facing the door. FIG. 18c shows a schematic representation of a carousel pharmaceutical dispensing machine. In these embodiments, the pharmaceutical array module 106, the pharmaceutical tote module 108 and the pharmaceutical operational modules section 110 are located on a column-type frame enabled to rotate on its axis. The mechanical arm module 112 is located on the side of the machine, and the rotation of the column-type frame brings the relevant modules in front of the mechanical arm module 112. Optionally, two mechanical arms are installed, for example, at 180 degrees to each other. In some embodiments, this configuration can be used for speeding up processes and/or for backup for the mechanical arm.

Exemplary Uses for Modular Pharmaceutical Dispensing Machines

In some embodiments, the modularity of the pharmaceutical dispensing machine can be used for more than just backup and/or redundancy in cases of technical malfunctions. In some embodiments, the modularity of the pharmaceutical dispensing machine is used to respond to demands and operational needs of the specific locations where the machines are located.

In some embodiments, examples of demands and/or needs may be, for example:

Different sizes of dispensing machines: a specific size of machine that can handle and storage a different amount of pills is provided according to the needs of the place. For example, machines that can handle 150 or 200 or 250 different types of pills can be provided by adding or removing specific modules.

Increase/Decrease in population: when a specific place suffers either an increase or a decrease in the population that requires the pharmaceutical dispensing service, different modules can be added/removed according to the change.

Multiple modules that perform the same task can have different configurations: for example, a dispensing machine that comprises two different envelope modules, each one with a different size of envelops can work simultaneously. In the case where one of the two sizes is not required, a module can be replaced so the two envelope modules comprise the same envelope size.

Easy upgradability: modules can be upgraded, either in their hardware or in their software, outside the dispensing machine, and the technician only needs to replace an old module with an upgraded module without the need to replace the whole pharmaceutical dispensing machine.

Easy to transport: separate small modules are transported more easily than whole machines.

Special size pills: in case a pharmaceutical dispensing machine requires to dispense a pill that has a special size, either bigger or smaller than the average pill size, a dedicated module/unit/element can be incorporated into the pharmaceutical dispensing machine without the need to replace the whole machine.

Different pill mix and amount of pills requires system adjustment

Modules can be tested remotely for diagnostics: besides the built-in diagnostic mechanism of the pharmaceutical dispensing machine, the modules can be monitored and/or diagnosed remotely from the main server, without the need to monitor and/or diagnose the whole machine.

In some embodiments, different sizes of pharmaceutical dispensing machines utilize the same modules. In some embodiments, the different modules are interchangeable between pharmaceutical dispensing machines of different sizes.

In some embodiments, the pharmaceutical dispensing machine uses redundancy of the modules, the units and the elements to perform the dispensing process. For example, in the cases where there are two mechanical arms, both mechanical arms are used to transport pharmaceuticals from their container (or multiple redundant containers containing the same and/or different pharmaceuticals) to the envelope (or multiple envelopes in the case where there are more than one envelope module).

Exemplary Methods

In some embodiments, the modules in the pharmaceutical dispensing machine do not work independently to each other. In some embodiments, the modules work as a series of actions performed by each module. For example, the control module receives information about the next batch of pharmaceuticals to be dispensed. The mechanical arm module is activated to reach for a specific pharmaceutical located in a drug unit located in the pharmaceutical array module. The pill is engaged by the pill engagement mechanism and the mechanical arm module transports the pharmaceutical to the envelope taken from the envelope module. Once all the necessary pharmaceutical are inserted in the envelope, the envelope is then closed, for example, by the crimper module, and the printer module marks the envelope with the relevant information. Then the mechanical arm module transports the envelope to the pharmaceutical tote module, where eventually a user will pick up the tray with all the envelopes.

In some embodiments, a user has discretion of deciding in what order the modules, units, elements and/or pharmaceuticals are used. In some embodiments, insertion of input regarding preferential order of activations of different components and/or pharmaceuticals is performed at the pharmaceutical dispensing machine itself via a display. In some embodiments, insertion of input regarding preferential order of activations of different components and/or pharmaceuticals is performed remotely by the user.

Referring now to FIG. 19, showing a schematic flowchart of a method performed by an exemplary pharmaceutical operation service system. In some embodiments, the dispensing machine runs a self-diagnostic program 200 on its software, hardware and inventory. In some embodiments, the dispensing machine might detect an issue 202 during the self-diagnostic program. In some embodiments, self-diagnostics are performed at given times (e.g. startup of machine, before each med run etc.). In some embodiments, diagnostic are performed upon some failure and/or schedule maintenance/diagnostic. In some embodiments, the machine comprises the option of remote diagnostics, in which the control center can interrogate the system and review all sensors and modules in order to assess their status. In some embodiments, the device comprises at least one camera on the arm module that can be moved remotely to see various elements of the machine. In some embodiments, the subcomponent and/or modules comprise at least one sensor and control logic for self-testing, for example, the rails will provide status report on their motors and encoders. In some embodiments, the operational modules are capable to detect, for example, low count on the consumables. In some embodiments, the at least one dedicated sensor and/or at least one camera are activated remotely by a user via a dedicated server. In some embodiments, issues revealed by the self-diagnostic program might be, for example, a technical issue 204, an inventory issue 206 and/or an unknown issue 208.

In some embodiments, statistics are used to anticipate and/or identify issues in the pharmaceutical dispensing machine. For example, modules that are used more often are more susceptible to technical issues and failures. In some embodiments, statistics and visual confirmation of issues are used to monitor the performance of the pharmaceutical dispensing machines.

In some embodiments, tests are used to monitor the performance of the pharmaceutical dispensing machine. In some embodiments, a user can remotely activate the pharmaceutical dispensing machine to prepare a mock envelope containing mock pharmaceuticals. The machines goes through the whole processing of picking the mock pharmaceutical, inserting it in an envelope, closing it and printing on it "mock" or "test". All this while observing via the cameras located in the different modules of the pharmaceutical dispensing machine, and monitoring the different sensors of each module.

In some embodiments, a cascade of inquiries is activated in each of the scenarios in order to assess the situation and proceed accordingly, as will be explained in the following paragraphs. In some embodiments, the dispensing machine continues the diagnostic program 210 either until it receives an "all ok" response or until the issue is detected and identified. In some embodiments, if the issue is and inventory issue 206, then the dispensing machine contacts the server 212 to solve the issue. In some embodiments, if the issue is, a technical issue 204 and/or an unknown issue 208, then a more specified identification of which module and/or unit and/or element has the issue 214. Once identified, the machine inquiries if there is a there a backup and/or redundant module and/or unit and/or element that can replace the affected module and/or unit and/or element 216. If there is not a backup and/or redundant module and/or unit and/or element that can replace the affected module and/or unit and/or element, then the machine contacts the server 218 to solve the issue. If there is a backup and/or redundant module and/or unit and/or element that can replace the affected module and/or unit and/or element, then (Flowchart continues following the letter A 220 to FIG. 20) the machine changes the primary module and/or unit and/or element to the backup and/or redundant module and/or unit and/or element and contacts the server 222 to notify the issue.

Referring now to FIG. 21 showing a schematic flowchart of an exemplary maintenance scheduling method for pharmaceutical operation service systems. In some embodiments, when a dispensing machine requires maintenance 230, the central server software brings up the estimated known time to perform maintenance to the modules/units/elements 232. Then, the central servers brings up the dispensing machine activity schedule 234. At this point, the software searches for a time window where all maintenance can be performed and the dispensing machine is inactive 236. If there is such time window, then the software schedules the maintenance 238. In some embodiments, there will be a follow up of the maintenance a period of time after the scheduled maintenance 240. In some embodiments, follow up is performed a day after the scheduled maintenance. Optionally can be a week after the scheduled maintenance. Optionally can be two weeks or more after the scheduled maintenance. If there is no such time window, (following letter "B" to FIG. 22), the software inquires if the maintenance can be divided in different time windows 242. If the answer is yes, then the maintenance tasks are divided and scheduled in different time windows 244. After that, a follow up will be done 246. If the maintenance cannot be divided then the software inquiries if the machine has backup and/or redundant hardware for the parts that require maintenance 248. If the answer is yes, then the software schedules the maintenance 250 since the backup and/or redundant hardware can be operated while performing the scheduled maintenance. After that, a follow up will be done 252. If the answer is no, (following letter "C" to FIG. 23), then the software chooses the least busy activity window in said dispensing machine activity schedule 254. Then the software schedules the maintenance and activates a secondary dispensing machine to provide pharmaceuticals during said least busy activity window where the maintenance is scheduled 256. After that, a follow up will be done 258.

EXAMPLES

Reference is now made to the following examples, which together with the above descriptions illustrate some embodiments of the invention in a non limiting fashion.

Preparation of a Batch of Pharmaceuticals

In a scenario of a hospital having several rooms in a floor, in each room several patients, it scheduled to deliver the morning medicines at 08:00 in the morning. The pharmaceutical dispensing machine receives the information regarding each patient, what medicine he/she needs to receive, in which bed is located in which room on the floor mentioned in the scenario. The pharmaceutical dispensing machine automatically commences the preparation of a batch of pharmaceuticals for the morning medicines for the patients calculating the required time to prepare all the pharmaceuticals. The pharmaceutical dispensing machine can prepare the batched per room and/or per floor and/or in the order of beds in each room on the floor. The mechanical arm module begins to pick up pills from the drug elements and transport them to the designated envelope. Once all the required pills are in the envelope, the envelope is closed and the information of the patient is printed on the envelope. Then the envelope is transported into the tray in the pharmaceutical tote module. This process goes on until all the envelopes containing all the pills for all the patients of the floor are ready. Then the user and/or the nurse picks up the tray, ready to be delivered according to the predetermined order.

Field Replacement of Modules

In a scenario where a pharmaceutical dispensing machine, having all the modules mentioned above and at least one redundant module for each module, is located in a hospital. During the preparation of a batch, the one of the envelope modules ceases to function. At this point, the pharmaceutical dispensing machine continues to operate utilizing only one envelope module. A signal is sent to the technician and/or a user that an envelope module is not working. For the sake of the scenario, a technician arrives with a brand new envelope module. While the pharmaceutical dispensing machine continues to prepare the batches of pharmaceuticals, the technician opens the machine, extracts the faulty envelope module and introduces the new envelope module at its place. All this while the pharmaceutical dispensing machine continues to prepare the pharmaceuticals to be delivered. The introduction of the new envelope module is received by the pharmaceutical operational modules section and the pharmaceutical dispensing machine begins using again both envelopes modules for the preparation of the batch. The same principle applies also to modules, hardware, units and elements.

Time/Production Optimization and Scheduling

In this scenario, a technician is required to schedule a maintenance in a pharmaceutical dispensing machine. The pharmaceutical dispensing machine already has the schedule for the preparation of the morning batch. The technician must perform the maintenance at a certain time, which coincides with the schedule of the preparation of the morning batch. In one scenario, the pharmaceutical dispensing machine can optimize the preparation of the morning batch by utilizing all available modules at its disposal. This way, for example, the pharmaceutical dispensing machine can prepare the batches in less time, therefore opening a window where the technician can come and perform the scheduled maintenance. In another scenario, the system can coordinate the maintenance with the preparation of the batches by using one set of modules while the technician performs maintenance on the other set of modules, and then, at a certain point, the roles change, the second set (already passed maintenance) works on preparing the batches while the first set is being maintained.

As used herein with reference to quantity or value, the term "about" means "within ±20% of".

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise. For example, the term "a unit" or "at least one unit" may include a plurality of units, including sub-units thereof.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A pharmaceutical dispensing machine configured to perform a pharmaceutical dispensing process including recovering at least one pharmaceutical from a dedicated container, relaying said at least one pharmaceutical to the inside of at least one pharmaceutical carrier package, closing and labeling said at least one pharmaceutical carrier package, and dispensing said at least one pharmaceutical inside said at least one pharmaceutical carrier package, comprising:
   a. at least one module configured in a first configuration to perform at least one first part of said pharmaceutical dispensing process;

b. dispensing hardware configured in a second configuration to perform at least one second part of said pharmaceutical dispensing process; and
c. circuitry which controls said recovering at least one pharmaceutical from a dedicated container, relaying said at least one pharmaceutical to the inside of at least one pharmaceutical carrier package, closing and labeling said at least one pharmaceutical carrier package, and dispensing said at least one pharmaceutical inside said at least one pharmaceutical carrier package; including coordinating the operation of said at least one module and said dispensing hardware using at least one parameter related to said dispensing pharmaceutical process;
wherein said at least one first part of said pharmaceutical dispensing process and said at least one second part of said pharmaceutical dispensing process overlap in functionality by at least one subassembly component in said dispensing hardware, which overlaps in functionality with said at least one module in said pharmaceutical dispensing process, and are performed at a same dispensing event, and
wherein said at least one module and said dispensing hardware are each configured to be independently dismounted from said pharmaceutical dispensing device while said pharmaceutical dispensing machine is operated and without interrupting said first or second part of said pharmaceutical dispensing process of said pharmaceutical dispensing machine.

2. The pharmaceutical dispensing machine of claim 1, wherein said at least one first part of said pharmaceutical dispensing process and said at least one second part of said pharmaceutical dispensing process are different parts of said pharmaceutical dispensing process.

3. The pharmaceutical dispensing machine of claim 1, wherein said at least one first configuration and said at least one second configuration are the same configuration.

4. The pharmaceutical dispensing machine of claim 1, wherein said at least one first configuration and said at least one second configuration are different configurations.

5. The pharmaceutical dispensing machine of claim 1, wherein said at least one first and said at least one second configuration are adapted for at least one parameter selected from the group consisting of:
a. type of pharmaceuticals;
b. size of pharmaceuticals;
c. quantity of pharmaceuticals;
d. type of pharmaceutical carrier packages;
e. size of pharmaceutical carrier packages;
f. engaging mechanism of pharmaceuticals; and
g. transporting mechanism of pharmaceuticals.

6. The pharmaceutical dispensing machine of claim 1, wherein said at least one first part of said pharmaceutical dispensing process and said at least one second part of said pharmaceutical dispensing process are performed at the same time.

7. The pharmaceutical dispensing machine of claim 1, wherein said at least one first part of said pharmaceutical dispensing process and said at least one second part of said pharmaceutical dispensing process are performed at different times.

8. The pharmaceutical dispensing machine of claim 1, wherein said at least one module is selected from a group consisting of: a pharmaceutical array module, a pharmaceutical tote module, a pharmaceutical operational modules section and a mechanical arm module.

9. The pharmaceutical dispensing machine of claim 8, wherein said pharmaceutical is recovered from said pharmaceutical array module by said mechanical arm module.

10. The pharmaceutical dispensing machine of claim 8, wherein said pharmaceutical is transported to an envelope located in an envelope module in said operational modules section by said mechanical arm module.

11. The pharmaceutical dispensing machine of claim 1, wherein said pharmaceutical dispensing process comprises at least one of the following:
a. inserting more than one pharmaceutical into one envelope;
b. inserting more than one type of pharmaceutical into one envelope;
c. inserting one type of pharmaceutical in more than one envelope.

12. The pharmaceutical dispensing machine of claim 1, wherein said dispensing hardware is operated when said at least one module cannot be operated.

13. The pharmaceutical dispensing device of claim 1, wherein said at least one module comprises at least one unit configured in a third configuration to perform at least one third part of said process; and said at least one unit comprises at least one element configured in a fourth configuration to perform at least one fourth part of said process.

14. The pharmaceutical dispensing machine of claim 1, wherein modules, hardware, units and elements comprise at least one additional hardware in communication with said circuitry and configured to monitor part of said process, selected from the group consisting of:
a. at least one sensor; and
b. at least one camera;
said at least one additional hardware is activated remotely by a user via a dedicated server.

15. The pharmaceutical dispensing machine of claim 1, wherein modules are configured to be independently replaced from said pharmaceutical dispensing device.

16. The pharmaceutical dispensing machine of claim 15, wherein replacing said modules does not interrupt the part of said process of said pharmaceutical dispensing machine.

17. The pharmaceutical dispensing machine of claim 15, wherein disconnecting between said modules and said pharmaceutical dispensing machine when replacing said modules takes from about 1 second to about 10 minutes.

18. The pharmaceutical dispensing device of claim 1, wherein said at least one module is activated at the middle of said pharmaceutical dispensing process.

19. The pharmaceutical dispensing device of claim 1, wherein said at least one dispensing hardware is activated at the middle of said pharmaceutical dispensing process.

20. A method of operating a pharmaceutical dispensing device comprising:
a. providing a pharmaceutical dispensing device with at least one first removable pharmaceutical dispensing module, at least one second removable pharmaceutical dispensing module and circuitry interconnecting, controlling and coordinating mechanical operations in a pharmaceutical dispensing process of said first and said second removable pharmaceutical dispensing modules using at least one parameter related to dispensing pharmaceuticals;
c. configuring, before a dispensing event, said at least one second removable pharmaceutical dispensing module to perform a mechanical operation of said at least one first removable pharmaceutical dispensing module;

d. mechanically operating said first and said second removable pharmaceutical dispensing modules at a same dispensing event;

e. continuing mechanically operating, during the same dispensing event, one of said modules when the other cannot operate;

wherein said method comprises independently dismounting said module that cannot operate while operating said pharmaceutical dispensing machine and without interrupting said mechanical operating of said pharmaceutical dispensing device at same said dispensing event.

21. The method of claim 20, providing said first and said second removable pharmaceutical dispensing modules from a group consisting of: a pharmaceutical array module, a pharmaceutical tote module, a pharmaceutical operational modules section and a mechanical arm module.

22. The method of claim 20, wherein said pharmaceutical dispensing process comprises:

a. storing at least one pharmaceutical;

b. receiving information of at least one pharmaceutical to be dispensed;

c. identifying said at least one pharmaceutical;

d. identifying at least one location of said at least one pharmaceutical;

e. collecting said at least one pharmaceutical from said at least one location;

f. transporting said at least one pharmaceutical from said at least one location to at least one secondary location in said dispensing machine;

g. releasing said at least one pharmaceutical in said at least one secondary location;

h. printing at least one information on at least one pharmaceutical transporting container;

i. closing said at least one pharmaceutical transporting container;

j. inserting said at least one container in at least one tote; and k. dispensing said at least one tote to at least one authorized user.

23. The method of claim 20, wherein said at least one parameter or said mechanical operation is selected from the group consisting of:

a. storing at least one pharmaceutical;

a. identifying at least one pharmaceutical;

b. identifying at least one location of said at least one pharmaceutical;

c. collecting said at least one pharmaceutical from said at least one location;

d. transporting said at least one pharmaceutical from said at least one location to at least one secondary location in said dispensing machine;

e. releasing said at least one pharmaceutical in said at least one secondary location;

f. printing at least one information on at least one pharmaceutical transporting container;

g. closing said at least one pharmaceutical transporting container;

h. inserting said at least one container in at least one tote; and i. dispensing said at least one tote to at least one authorized user.

24. The method of claim 23, wherein said at least one location is located in said pharmaceutical array module.

25. The method of claim 20, wherein said transporting is performed by said mechanical arm module.

26. The method of claim 23, wherein said at least one secondary location is a pharmaceutical transporting container.

27. The method of claim 23, wherein said pharmaceutical transporting container is an envelope.

28. The method of claim 20, wherein said method comprises at least one of the following:

a. inserting more than one pharmaceutical into one envelope;

b. inserting more than one type of pharmaceutical into one envelope;

c. inserting one type of pharmaceutical in more than one envelope.

29. The pharmaceutical dispensing device of claim 1, wherein said pharmaceutical dispensing machine comprises all of said at least one module, said dispensing hardware and said circuitry in the same machine.

\* \* \* \* \*